United States Patent [19]
Saito et al.

[11] Patent Number: 5,705,452
[45] Date of Patent: Jan. 6, 1998

[54] SULFONYL COMPOUND AND THERMAL-SENSITIVE RECORDING MEDIUM USING THE SAME

[75] Inventors: Toranosuke Saito; Shigeru Oda; Eiji Kawabata, all of Ibaraki, Japan

[73] Assignee: Sanko Haihatsu Kagaku Kenkyusho, Ibaraki, Japan

[21] Appl. No.: 540,722

[22] Filed: Oct. 11, 1995

[30] Foreign Application Priority Data

Oct. 14, 1994 [JP] Japan .................................. 6-249265
Jan. 30, 1995 [JP] Japan .................................. 7-012134

[51] Int. Cl.$^6$ .................................................. B41M 5/30
[52] U.S. Cl. .................................................. 503/216; 427/150
[58] Field of Search .................................... 427/150, 151; 503/216, 217, 225

[56] References Cited

U.S. PATENT DOCUMENTS 5,420,094   5/1995   Araki et al. .................................. 503/216

FOREIGN PATENT DOCUMENTS

| 0 131 631 | 1/1985 | European Pat. Off. | 503/216 |
| 0 183 275 | 6/1986 | European Pat. Off. | 503/216 |
| 0 466 096 A1 | 1/1992 | European Pat. Off. | 503/216 |
| 0 563 392 A1 | 10/1993 | European Pat. Off. | 503/216 |
| 0 567 314 A1 | 10/1993 | European Pat. Off. | 503/216 |
| 0 623 594 A1 | 11/1994 | European Pat. Off. | 503/216 |
| 3-140290 | 6/1991 | Japan | 503/216 |
| 4-344286 | 11/1992 | Japan | 503/216 |
| 5-64966 | 3/1993 | Japan | 503/216 |
| 2 142 630 | 1/1985 | United Kingdom | 503/216 |
| 2 154 236 | 9/1985 | United Kingdom | 503/216 |

OTHER PUBLICATIONS

European Search Report No. EP 95116182 and Communication dated Feb. 21, 1996.
Journal of Organic Chemistry of the USSR, p. 2406.
Chemical Abstracts—Eleventh Collective Index. vols. 96–105 (1982–1986).

Primary Examiner—Bruce H. Hess
Attorney, Agent, or Firm—Kane, Dalsimer, Sullivan, Kurucz, Levy, Eisele and Richard, LLP

[57] ABSTRACT

A thermal recording medium comprising a as a developer a sulfonyl compound represented by general formula (1) or a polyvalent metal salt thereof.

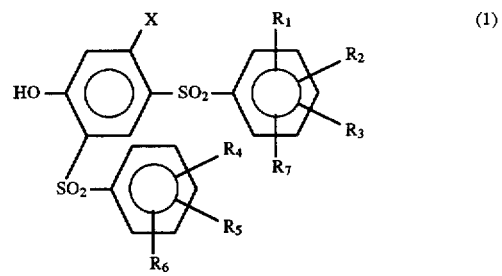

where X represents H or a lower alkyl group, $R_1$, $R_2$ and $R_3$ represent H, halogen atom, a hydroxyl group, a lower alkyl group or a cycloalkyl group, $R_4$, $R_5$ and $R_6$ represent H, halogen atom, a lower alkyl group or a cycloalkyl group, and $R_7$ represents H or

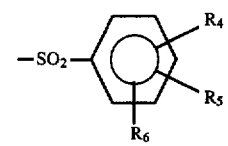

where $R_4$, $R_5$ and $R_6$ are as defined above. The thermal recording medium has a high sensitivity and a lower background blush during storage, and also has excellent stability against heating, moisture and plasticizer.

2 Claims, 16 Drawing Sheets

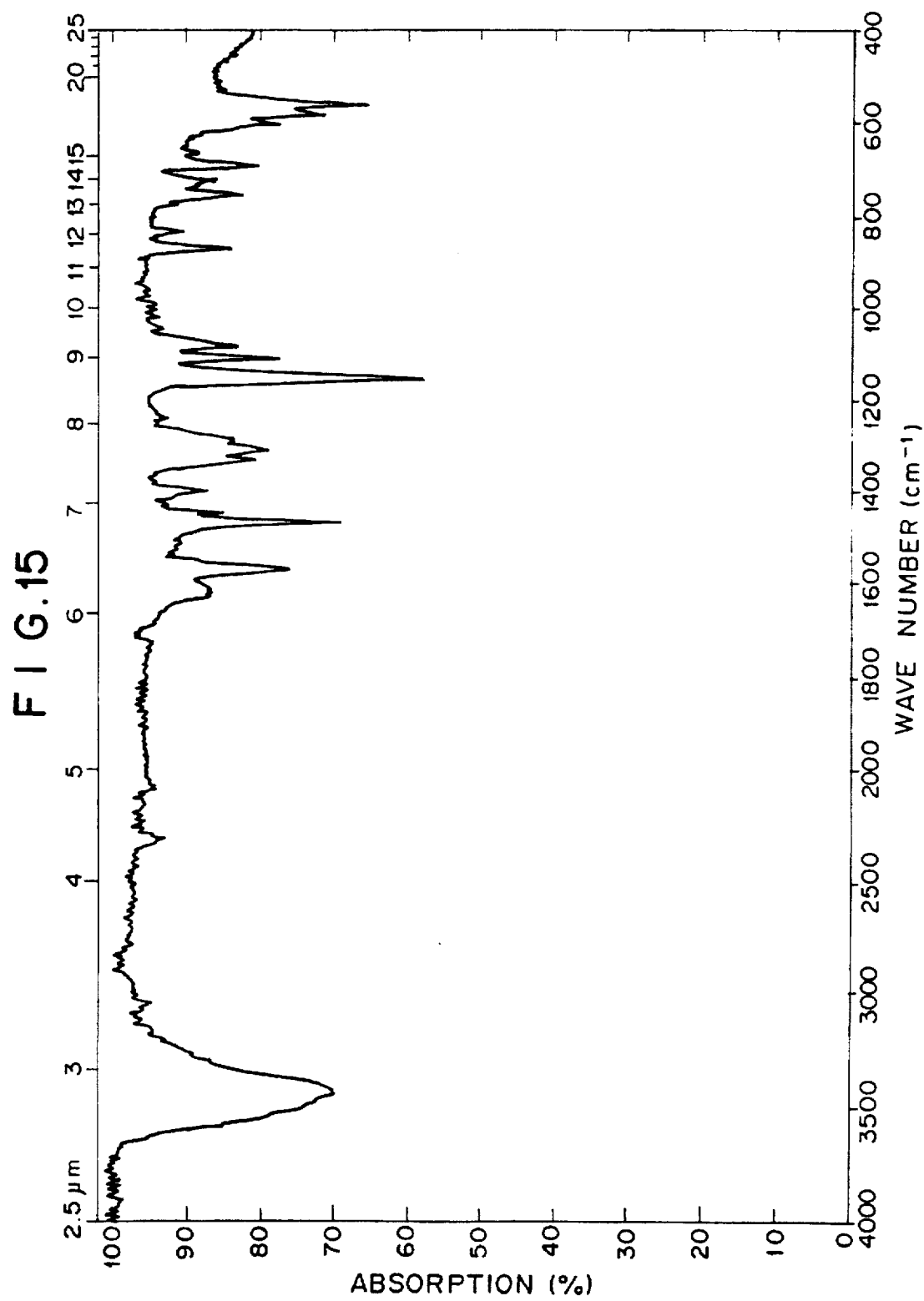

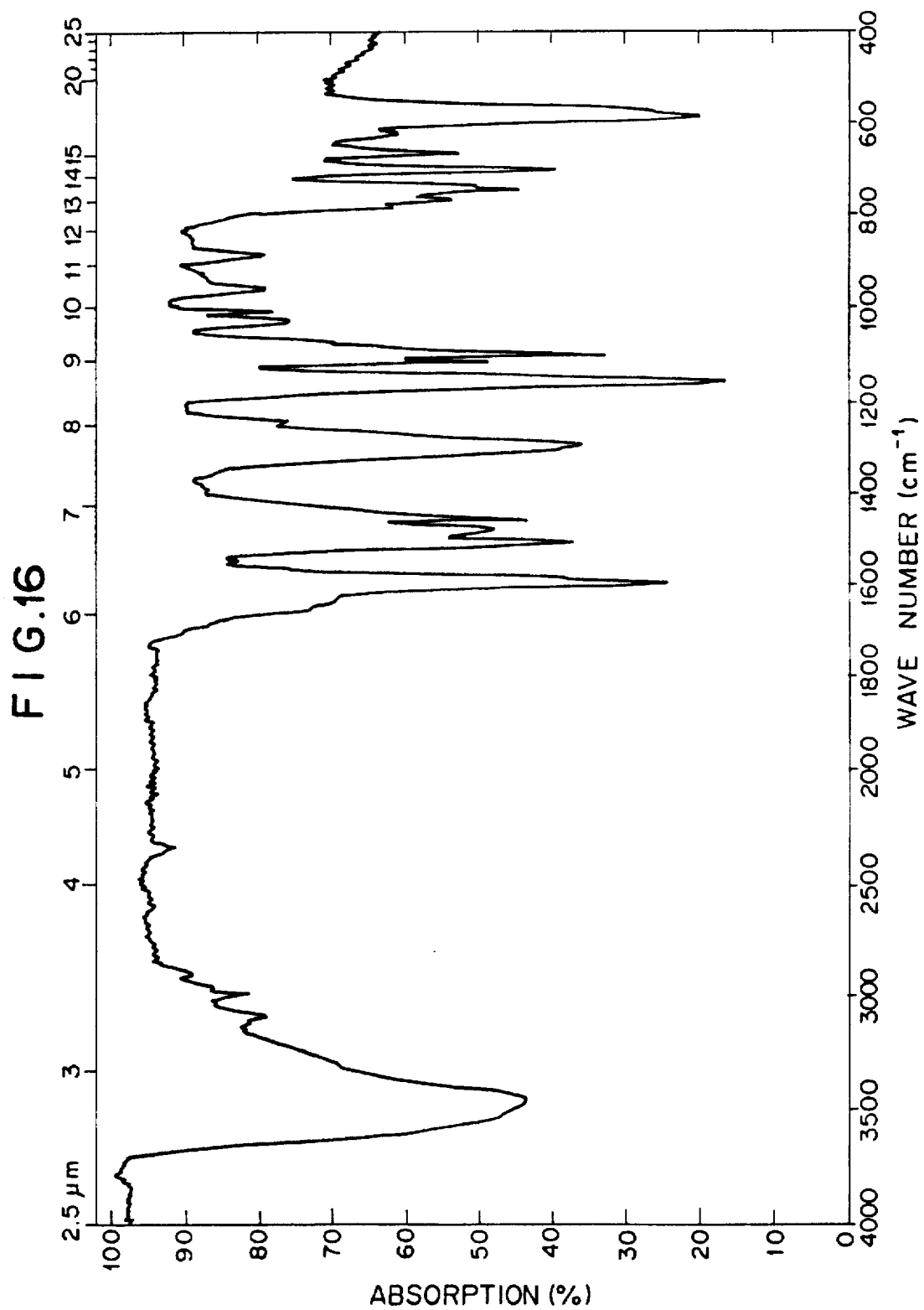

SULFONYL COMPOUND AND THERMAL-SENSITIVE RECORDING MEDIUM USING THE SAME

BACKGROUND OF THE INVENTION

1. Field of the Invention

The present invention relates to a specific sulfonyl compound and a polyvalent metal salt thereof, and to the usage of the compounds, more particularly to specific a sulfonyl compound and a polyvalent metal salt thereof, which, when used as a developer, provide a thermal recording medium having less blushing on the background and storage stability of the recorded image especially under the humid condition, thermal resistance and durability against a plasticizer.

2. Prior Art

Thermal recording media using a thermal developing reaction of a basic dye precursor and an electron receptive developer have heretofore been well known. As a developer for those media, 2,2-bis(4-hydroxyphenyl)propane and 4-hydroxy-4'isopropoxydiphenylsulfone have been well known (see JPB Hei 3-54655, etc.).

However, the thermal recording media using the above developer has been recognized to be further improved in the storage stability of the recorded image especially under the humid condition, and also in the thermal resistance and durability against plasticizer.

SUMMARY OF THE INVENTION

It is an object of the present invention to provide a developer, which, when used as a developer, provides a thermal recording medium having less blushing on the background and storage stability of the recorded image especially under the humid condition, thermal resistance and durability against plasticizer.

We have found that, as a result of evaluation to find out a developer having a higher sensitivity and durability of recorded image, specific sulfonyl compounds and polyvalent metal salts thereof represented by general formula (1) below can satisfy the above requirement.

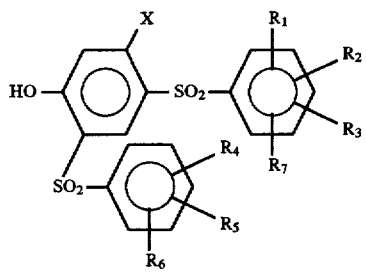

(1)

where X represents a hydrogen atom or a lower alkyl group, $R_1$, $R_2$ and $R_3$, which may be equal or different, represent a hydrogen atom, halogen atom, a hydroxyl group, a lower alkyl group or a cycloalkyl group, $R_4$, $R_5$ and $R_6$, which may be equal or different represent a hydrogen atom, halogen atom, a lower alkyl group or a cycloalkyl group, and $R_7$ represents a hydrogen atom or

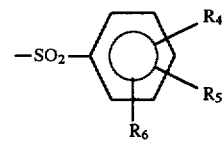

where $R_4$, $R_5$ and $R_6$ are as defined above.

BRIEF DESCRIPTION OF THE DRAWINGS

FIG. 15 is an infrared absorption spectrum of the compound obtained in Example 15; and FIG. 16 is an infrared absorption spectrum of the compound obtained in Example 16.

DETAILED DESCRIPTION OF THE INVENTION

Figure 1:
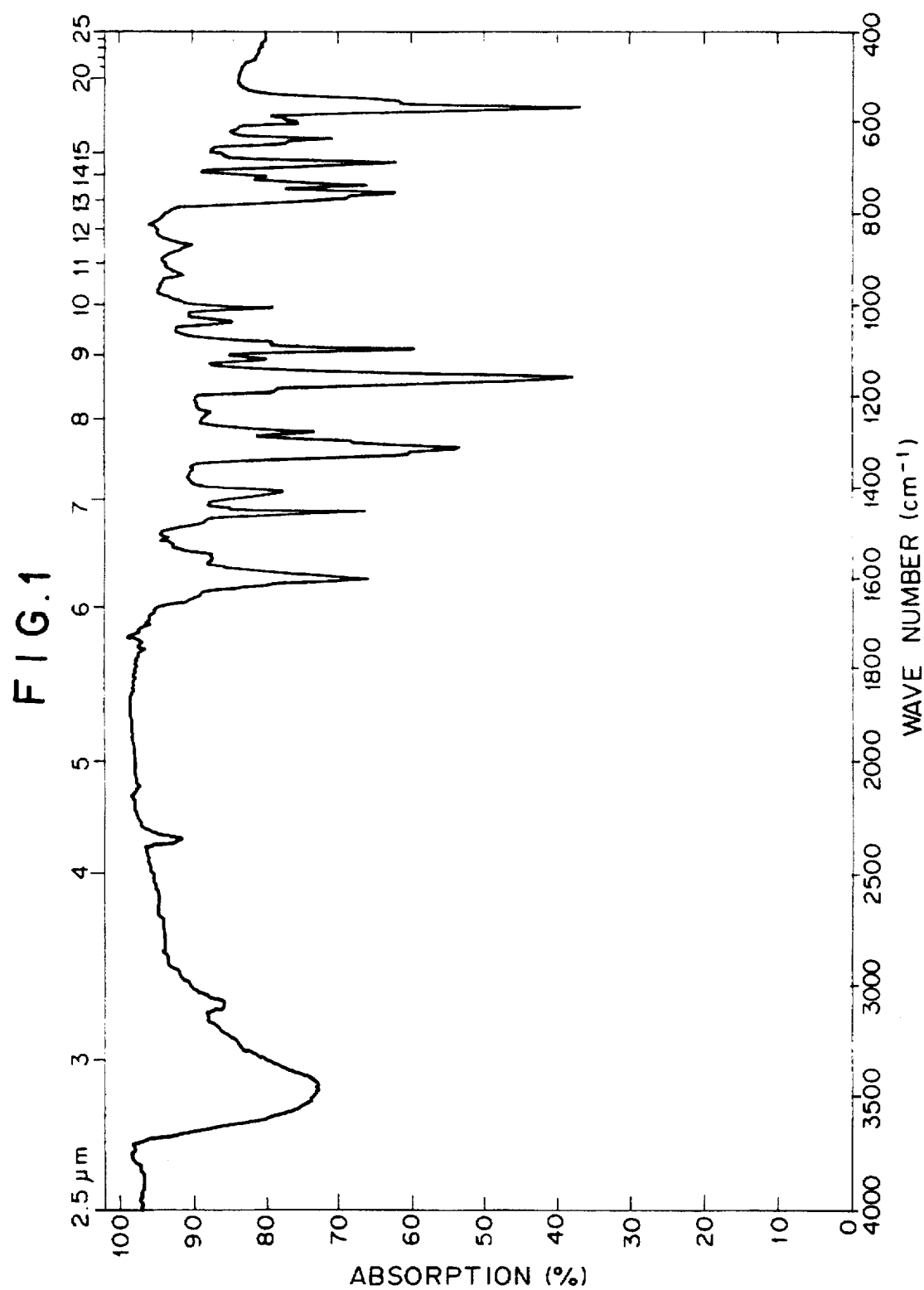
FIG. 1 is an infrared absorption spectrum of the compound obtained in Example 1.

The present invention relates to a thermal recording medium characterized by comprising the sulfonyl compounds or polyvalent metal salts thereof represented by general formula (1) as a developer. In general formula (1), the lower alkyl group has preferably 1 to 4 carbon atoms. Specific examples of the compounds represented by general formula (1) may include the following:

(1) 2,4-bis(phenylsulfonyl)phenol
(2) 2,4-bis(2-methylphenylsulfonyl)phenol
(3) 2,4-bis(4-ethylphenylsulfonyl)phenol
(4) 2,4-bis(4-bromophenylsulfonyl)phenol
(5) 2,4-bis(4-chlorophenylsulfonyl)phenol
(6) 2,4-bis(2,4-dimethylphenylsulfonyl)phenol
(7) 2,4-bis(3,4-dimethylphenylsulfonyl)phenol
(8) 2,4-bis(2,5-dimethylphenylsulfonyl)phenol
(9) 2,4-bis(2,4,6-trimethylphenylsulfonyl)phenol
(10) 2,4-bis(4-ethylphenylsulfonyl)phenol
(11) 2,4-bis(4-isopropylphenylsulfonyl)phenol

(12) 2,4-bis(4-cyclohexylphenylsulfonyl)phenol
(13) 2,4-bis(phenylsulfonyl)-5-methylphenol
(14) 2,4-bis(2-methylphenylsulfonyl)-5-methylphenol
(15) 2,4-bis(4-methylphenylsulfonyl)-5-methylphenol
(16) 2,4-bis(4-isopropylphenylsulfonyl)-5-methylphenol
(17) 2,4-bis(2,4-dimethylphenylsulfonyl)-5-methylphenol
(18) 2,4-bis(2,5-dimethylphenylsulfonyl)-5-methylphenol
(19) 2,4-bis(phenylsulfonyl)-5-ethylphenol
(20) 2,4-bis(4-methylphenylsulfonyl)-5-ethylphenol
(21) 2,4-bis(4-ethylphenylsulfonyl)-5-ethylphenol
(22) 2,4-bis(2,4-dimethylphenylsulfonyl)-5-ethylphenol
(23) 2,4-bis(2,5-dimethylphenylsulfonyl)-5-ethylphenol
(24) 2,4-bis(phenylsulfonyl)-5-isopropylphenol
(25) 2-(4-methylphenylsulfonyl)-4-(phenylsulfonyl)phenol
(26) 2-(4-ethylphenylsulfonyl)-4-(phenylsulfonyl)phenol
(27) 2-(4-isopropylphenylsulfonyl)-4-(phenylsulfonyl)phenol
(28) 2-(2,5-dimethylphenylsulfonyl)-4-(phenylsulfonyl)phenol
(29) 2-(2,4-dimethylphenylsulfonyl)-4-(phenylsulfonyl)phenol
(30) 2-(3,4-dimethylphenylsulfonyl)-4-(phenylsulfonyl)phenol
(31) 2-(4-chlorophenylsulfonyl)-4-(phenylsulfonyl)phenol
(32) 2-(4-bromophenylsulfonyl)-4-(phenylsulfonyl)phenol
(33) 2-(phenylsulfonyl)-4-(4-methylphenylsulfonyl)phenol
(34) 2-(phenylsulfonyl)-4-(4-ethylphenylsulfonyl)phenol
(35) 2-(phenylsulfonyl)-4-(4-isopropylphenylsulfonyl)phenol
(36) 2-(phenylsulfonyl)-4-(2-methylphenylsulfonyl)phenol
(37) 2-(phenylsulfonyl)-4-(2,5-dimethylphenylsulfonyl)phenol
(38) 2-(phenylsulfonyl)-4-(2,4-dimethylphenylsulfonyl)phenol
(39) 2-(phenylsulfonyl)-4-(3,4-dimethylphenylsulfonyl)phenol
(40) 2-(phenylsulfonyl)-4-(4-chlorophenylsulfonyl)phenol
(41) 2-(phenylsulfonyl)-4-(4-bromophenylsulfonyl)phenol
(42) 2-(4-methylphenylsulfonyl)-4-(phenylsulfonyl)-5-methylphenol
(43) 2-(4-chlorophenylsulfonyl)-4-(phenylsulfonyl)-5-methylphenol
(44) 2-(4-bromophenylsulfonyl)-4-(phenylsulfonyl)-5-methylphenol
(45) 2-(phenylsulfonyl)-4-(methylphenylsulfonyl)-5-methylphenol
(46) 2-(phenylsulfonyl)-4-(4-chlorophenylsulfonyl)-5-methylphenol
(47) 2-(phenylsulfonyl)-4-(4-bromophenylsulfonyl)-5-methylphenol
(48) 2-(4-methylphenylsulfonyl)-4-(phenylsulfonyl)-5-ethylphenol
(49) 2-(4-chlorophenylsulfonyl)-4-(phenylsulfonyl)-5-ethylphenol
(50) 2-(4-bromophenylsulfonyl)-4-(phenylsulfonyl)-5-ethylphenol
(51) 2-(phenylsulfonyl)-4-(4-methylphenylsulfonyl)-5-ethylphenol
(52) 2-(phenylsulfonyl)-4-(4-chlorophenylsulfonyl)-5-ethylphenol
(53) 2-(phenylsulfonyl)-4-(4-bromophenylsulfonyl)-5-ethylphenol
(54) 2-(4-methylphenylsulfonyl)-4-(phenylsulfonyl)-5-isopropylphenol
(55) 2-(phenylsulfonyl)-4-(4-methylphenylsulfonyl)-5-isopropylphenol
(56) 4,4'-dihydroxy-5-(phenylsulfonyl)diphenylsulfone
(57) 4,4'-dihydroxy-5,5'-bis(phenylsulfonyl)diphenylsulfone
(58) 4,4'-dihydroxy-5-(4-chlorophenylsulfonyl)diphenylsulfone
(59) 4,4'-dihydroxy-5,5'-bis(4-methylphenylsulfonyl)diphenylsulfone
(60) 4,4'-dihydroxy-5,5'-bis(4-chlorophenylsulfonyl)diphenylsulfone
(61) 4,4'-dihydroxy-5,5'-bis(4-bromophenylsulfonyl)diphenylsulfone Of the sulfonyl compounds listed above, compounds (1), (3), (5)–(8), (10)–(11), (13), (15), (19), (25)–(26), (28)–(31), (33)–(34), (37)–(40), and (56)–(57) are of more preferable. Preferable examples of metals which are used to constitute a polyvalent salts with the above compounds include: zinc, magnesium, strontium, aluminum, iron, cobalt, nickel and titanium. The most preferable metals are zinc, magnesium, aluminum, iron, nickel and titanium.

Referring now to the method of preparation of sulfonyl compound, the following three reactions conducted under the presence of the Friedel-Crafts catalyst are applicable:

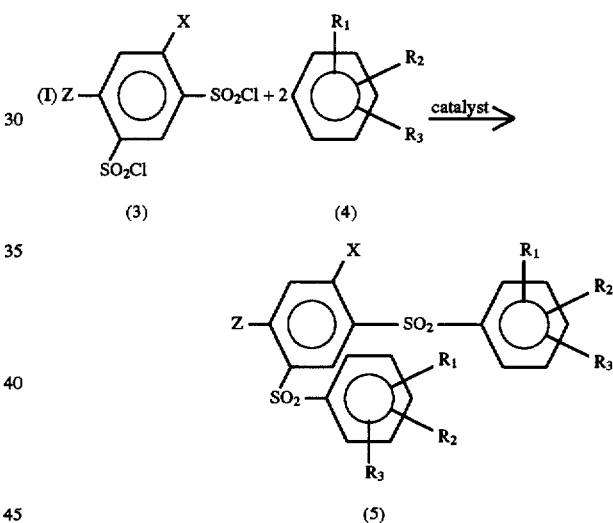

In general formula (3), Z represents a halogen atom, and X is as defined in general formula (1). In general formula (4), $R_1$, $R_2$ and $R_3$ are as defined in general formula (1). In general formula (5), Z is as defined in general formula (3), and X, $R_1$, $R_2$ and $R_3$ are as defined in general formula (1).

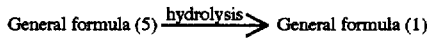

When this method is used, in general formula (1),

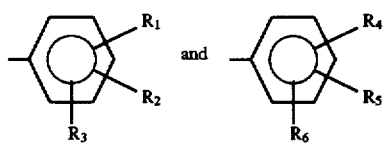

are same, and $R_7$ is a hydrogen atom.

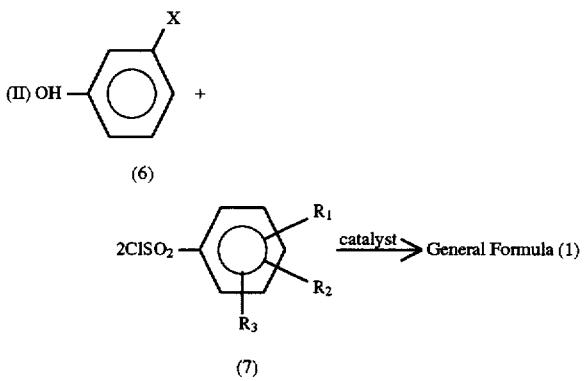

In general formula (6), X is as defined in general formula (1). In general formula (7), $R_1$, $R_2$ and $R_3$ are as defined in general formula (1). But, when this method is used, general formula (1) is as defined in method (I).

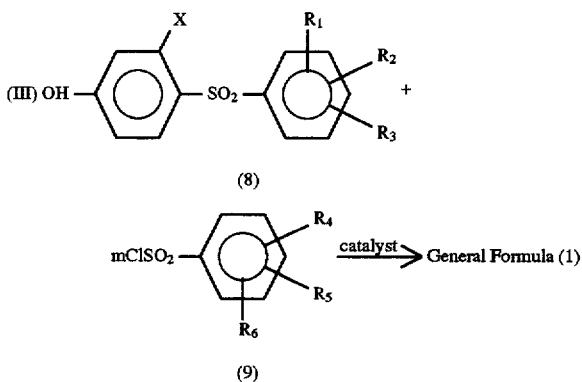

In general formula (8), X, $R_1$, $R_2$ and $R_3$ are as defined in general formula (1). In general formula (9), m represents 1 or 2, and $R_4$, $R_5$ and $R_6$ are as defined in general formula (1).

In this reaction, the catalyst is selected from the Friedel-Crafts catalysts. Preferable examples of such catalysts may include iron chloride, aluminum chloride, zinc chloride, magnesium chloride and so on.

As has been mentioned above, the thermal recording medium of the present invention is characterized by that, in a thermal recording medium comprising a substrate and a thermal recording layer containing an electron donative basic dye precursor, the thermal recording layer comprises an electron receptible developer and a sensitizer, a compound represented by general formula (1) or a polyvalent metal salt thereof alone or in any combination, and a combination of at least one of the developer and at least one of diphenyl derivatives represented by general formula (2) below:

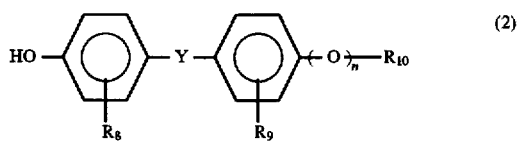

where $R_8$ and $R_9$, which may be equal or different, represent a hydrogen atom, a lower alkyl group or a lower alkylene group, and $R_{10}$ represents a hydrogen atom or straight or branched lower alkyl group, Y represents sulfonyl group, a lower alkylene group or a lower alkylidene group, and n represents 0 or 1.

In the definition of general formula (2), the lower alkyl group includes preferably 1–4 carbon atoms, and the lower alkylene group includes preferably 1–4 carbon atoms.

The diphenyl derivatives represented by general formula (2) may, for example, be 2,2-bis(4-hydroxyphenyl)propane, 4-hydroxy-4'-isopropoxydiphenylsulfone, 4,4'-dihydoxydiphenylsulfone, bis(3-aryl-4-hydroxyphenyl)sulfone, 4-hydroxy-2'-5'-dimethyldiphenylsulfone, 2-methyl-4-hydroxydiphenylsulfone and the like.

Next, a suitable combination of the compound of the present invention as a developer will be described in more detail.

(1) It is preferable that the number of the compounds used in combination is 2 or 3, because a larger number than this would cause handling difficult.

(2) For achieving the purpose of the present invention, the sulfonyl compound represented by general formula (1) is essential.

(3) The least content of each compound is 1 part by weight, preferably 5 parts by weight or more on the basis of 100 parts by weight of the total amount of the developer.

(4) As a method of blending, either one of the following methods can be applied: (a) blending the desired compounds, which have previously been pulverized, in a desired ratio; (b) blending the compounds in a desired ratio and then pulverizing the blend; and (c) preparing a blend consisting of the compounds in a desired ratio by recrystallization and then pulverizing the blend.

The polyvalent metal salts used as a developer may be prepared by reacting the compound represented by general formula (1) with a soluble salt of a polyvalent metal such as zinc, magnesium, strontium, aluminum, iron, cobalt, nickel and titanium. Alternatively, the polyvalent metal may be coexistent with the compound represented by general formula (1) in a thermal recording layer in the form of oxide, hydroxide, carbonate, sulfonate or the like. When used as a developer, the total amount of the polyvalent metal salts may preferably be 50–600 parts, more preferably 100–400 parts by weight per 100 parts by weight of the basic dye.

The basic dye and the sensitizer used in the recording medium of the present invention will be described below.

Examples of the basic dye may include triaryl methanes, diaryl methanes, pyridines, spiro-series compounds, rhodamine-lactam compounds, fluoranes, indolylphthalides and fluolenes. Typical compounds of the above are 3-N,N-dibutylamino-6-methyl-7-anilinofluorane, 3-N,N-diethylamino-6-methyl-7-anilinofluorane, 3-(N-isopentyl-N-ethyl)-6-methyl-7-anilinofluorane, 3-(N-cyclohexyl-N-methyl)-6-methyl-7-anilinofluorane, and 3-N,N-diethyl-6-chloro-7-anilinofluorane. These basic dyes can be used alone or in any combination for the purpose of adjusting the color of the image or polychrome thermal recording media.

Examples of the sensitizer may include esters, hydrocarbons, ethers and sulfones. Typical examples are beta-naphtylbenzylether, stearic amides, 4-benzyloxybenzoic benzyl ester, oxalic dibenzyl, oxalic-di-P-methylbenzyl, bis(4-methylphenyl)carbonate, 4-benzylbiphenyl, N-terphenyl, 1,2-bis(3-metylphenoxy)ethane, 1,2-bis(phenoxy)ethane, diphenylsulfone and 3,3',4,4'-tetramethyl-diphenylethane. These sensitizers can be used alone or in any combination. Further, the amount of the sensitizers is preferably 50–800 parts, more preferably 100–400 parts by weight per 100 parts by weight of the basic dye.

The thermal recording medium can be manufactured in accordance with any well known process, and there is no need to use any special process. In general, a basic dye, a developer, a sensitizer, a pigment, a metal soap, a wax, a surfactant, an antifoaming agent etc. are dispersed in an aqueous medium containing a water soluble binder and pulverized by means of a ball mill or a sand mill into usually 3 μm or less, more preferably 1.5 μm or less to obtain a coating liquid.

Examples of pigments may include potassium carbonate, magnesium carbonate, titanium oxide, kaolin, silica, amorphous silica zinc oxide and the like.

Examples of metal soaps may include zinc stearate and calcium stearate.

Examples of waxes may include paraffine wax, microcrystalline wax, polyethylene wax and the like.

Examples of surfactants may include alkali metal salts of sulfosuccinic acid, alkali metal salts of alkylbenzenesulfonic acid, sodium salts of lauryl alcohol sulfonic acid esters and the like.

In the thermal recording medium of the present invention, the thermal recording layer can be formed in any well known process, and there is no limitation for the forming process. For example, the coating liquid for the thermal recording layer may be applied by means of an air knife coater, a blade coater, a bar coater, a gravure coater, a curtain coater, a wire bar and the like, and then dried. There is no limitation for the amount of the coating liquid to be applied, but a preferable amount may be 0.5–12 g/m$^2$, and more preferably be 1.0–8.0 g/m$^2$ on dry basis. The substrate is preferably a paper sheet, a plastic sheet or a synthetic paper sheet.

The present invention will be more clearly understood from the following specific examples.

EXAMPLE 1

A 2 liter reaction vessel was charged with 309 g of 1-chloro-2,4-sulfonylbenzen dichloride, 20 g of benzene and 2 g of anhydrous ferric chloride. The charge was heated with stirring to 150° C. in a nitrogen atmosphere, into which 150 g of benzene was dropped over 20 hours at the same temperature. During the dropping crystals were formed. After completion of the dropping, the reaction mixture was allowed to stand for 2 hours at the same temperature for aging, and then 500 g of benzene was poured slowly. The reaction mixture was then cooled to a room temperature, and the crystals formed therein was filtered out of the mixture. The crystals were washed with 1 liter of methanol to obtain 280 g of white crystal powder having a melting point of 196° C.

Next, 196 g of the crystal powder and 600 g of 10% aqueous sodium hydroxide solution were charged into an autoclave reactor, and heated at a temperature of 200° C. under a pressure of 15 kg/cm$^2$ for 5 hours for hydrolysis. After being cooled, an amount of 10% dilute sulfuric acid was slowly dropped with stirring to bring pH 6. The crystals thus formed were filtered out, and then purified by recrystallization in n-butanol to obtain 160 g of white crystal powder having a melting point of 157° C. From the results of the IR analysis, NMR analysis and elementary analysis (Table 1), it was confirmed that the product was 2,4-bis (phenylsulfonyl)phenol.

TABLE 1

| Elementary Analysis Value (%) | C | H | S |
|---|---|---|---|
| Measured Value | 57.6 | 3.8 | 17.0 |
| Calculated Value (as C$_{18}$H$_{14}$O$_5$So$_2$) | 57.7 | 3.8 | 17.1 |

(Potassium bromide method. Same method was used in all the following Examples.)

The infrared absorption spectrum of the product is shown in FIG. 1. In FIGS. 1–16, the cordinates represent a rate of transmission (%) and the abscissas represent a wave number (cm$^{-1}$).

EXAMPLE 2

An 1 liter reaction vessel was charged with 94 g of phenol and 1 g of anhydrous ferric chloride. The charge was heated with stirring to 80° C. and 379 g of benzensulfonyl chloride was dropped into the charge over 2 hours at the same temperature. After completion of the dropping, the reaction mixture was allowed to stand at the same temperature for 5 hours, and then heated slowly to 150° C. and kept at this temperature for 24 hours for completion of the reaction.

Next, the reaction liquid thus obtained was poured into 1000 g of 5% aqueous sodium hydroxide solution, and the mixture was heated at 95° C. for 2 hours with stirring, and then filtered. The filtrate was then slowly dropped into 1000 g of 6% dilute sulfuric acid kept at 90° C. with stirring, thereby to obtain crystals. The crystals were filtered out, and after washed with 1 liter of water, dissolved in 1 liter of warm methylisobutylketone, and then 100 ml of water was added to wash out an oily component. The oily component was separated out, and further washed with 100 ml of water two times. Then, water in the oily component was removed by azeotropy, and the remaining component was subjected to decoloring by 3 g of activated carbon and 1 g of activated clay. The solution thus obtained was cooled to a room temperature to obtain 310 g of white crystal powder having a melting point of 157° C. From the results of the IR analysis, NMR analysis and elementary analysis (Table 2), it was confirmed that the product was 2,4-bis (phenylsulfonyl)phenol.

TABLE 2

| Elementary Analysis Value (%) | C | H | S |
|---|---|---|---|
| Measured Value | 57.8 | 3.8 | 17.0 |
| Calculated Value (as C$_{18}$H$_{14}$O$_5$S$_2$) | 57.7 | 3.8 | 17.1 |

Figure 2:
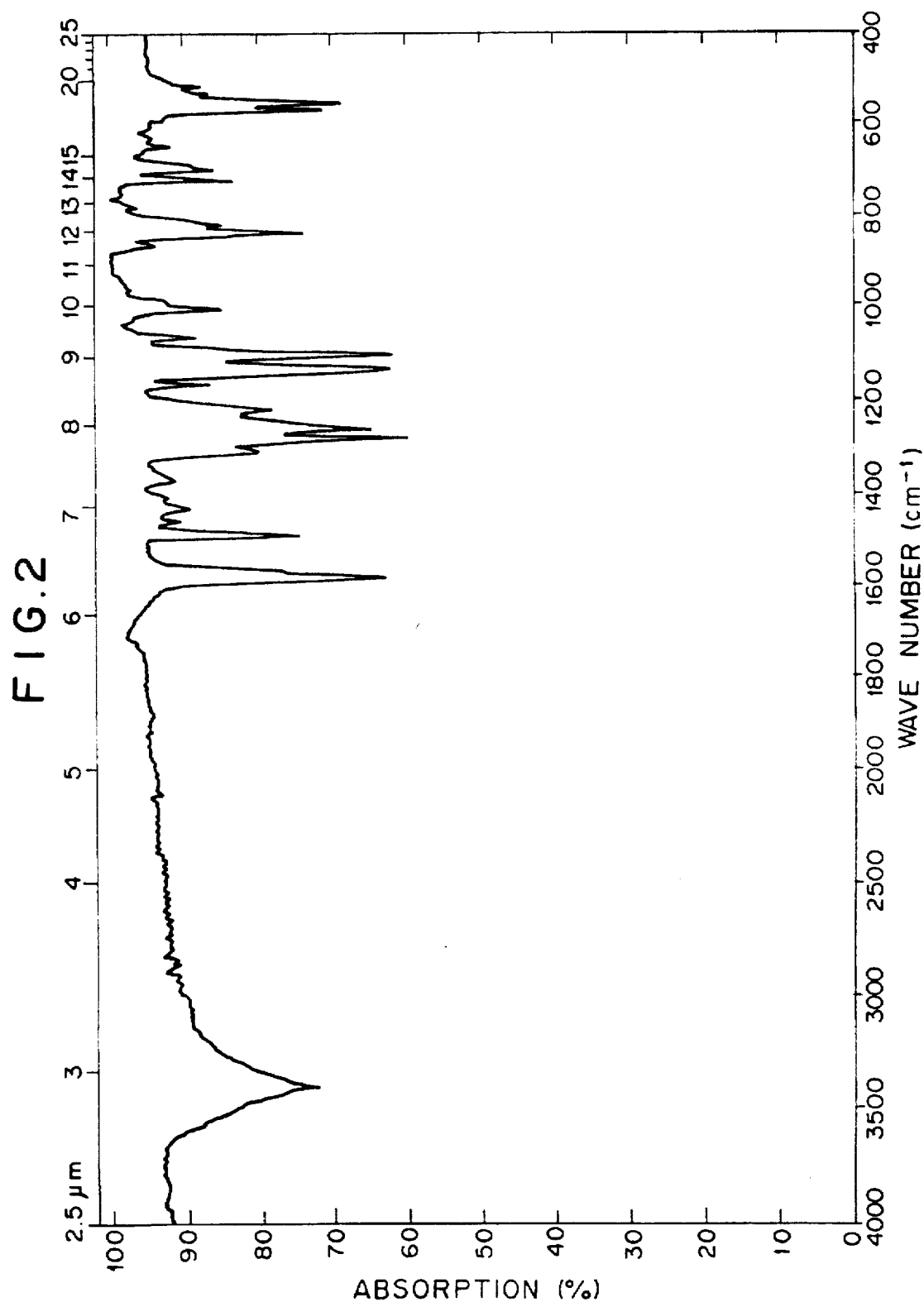
FIG. 2 is an infrared absorption spectrum of the compound obtained in Example 2.
Figure 3:
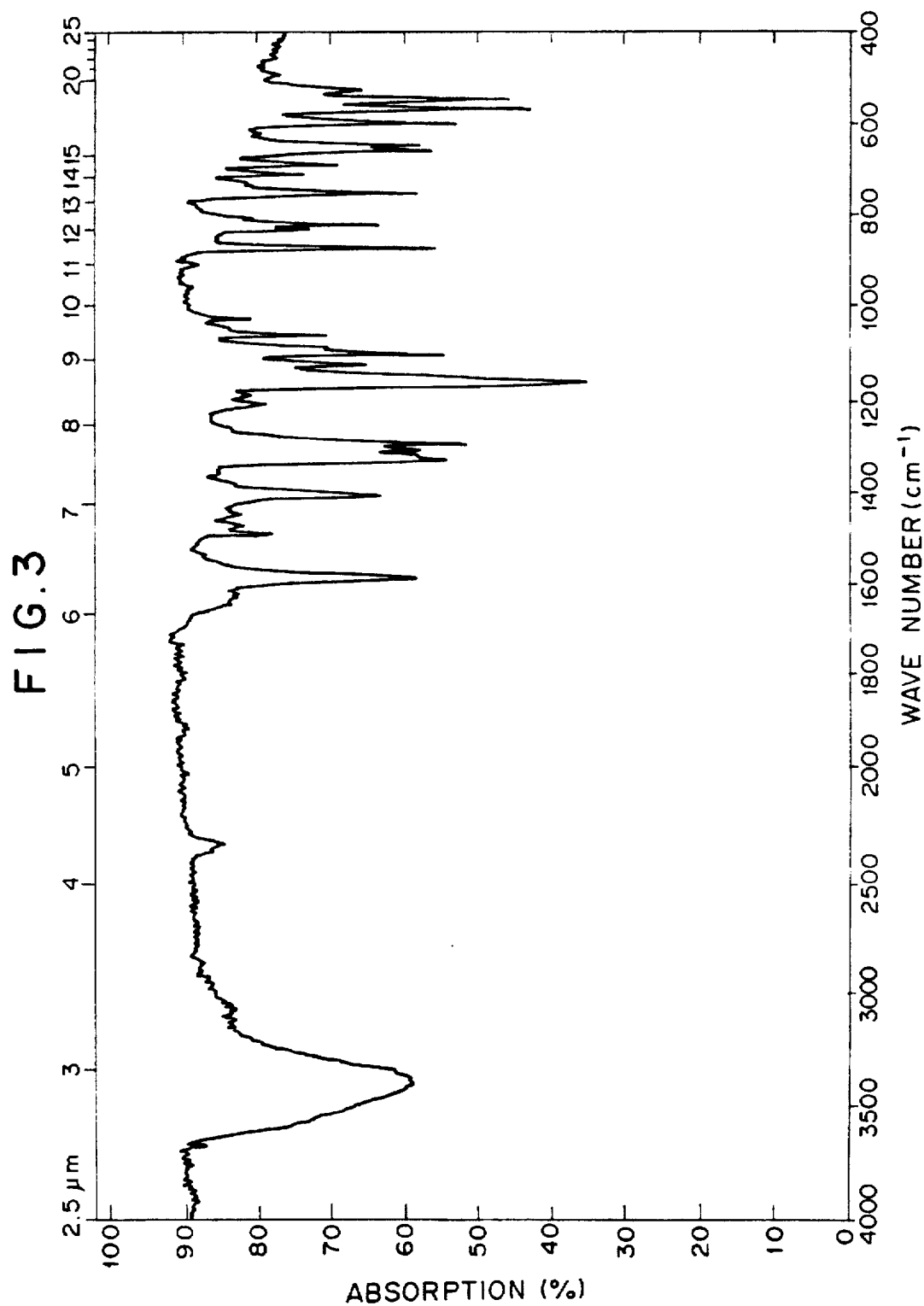
FIG. 3 is an infrared absorption spectrum of the compound obtained in Example 3.
Figure 4:
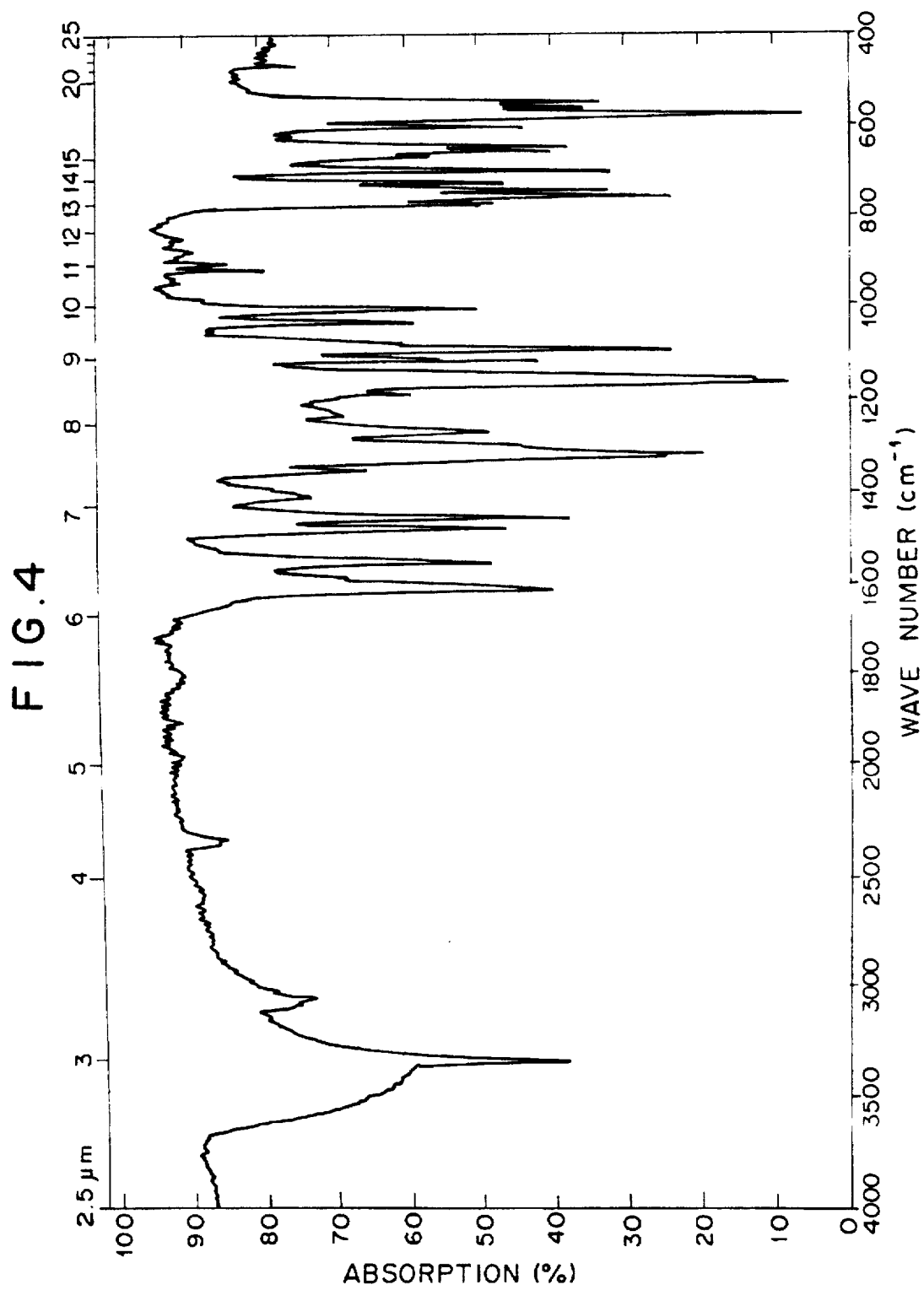
FIG. 4 is an infrared absorption spectrum of the compound obtained in Example 4.
Figure 5:
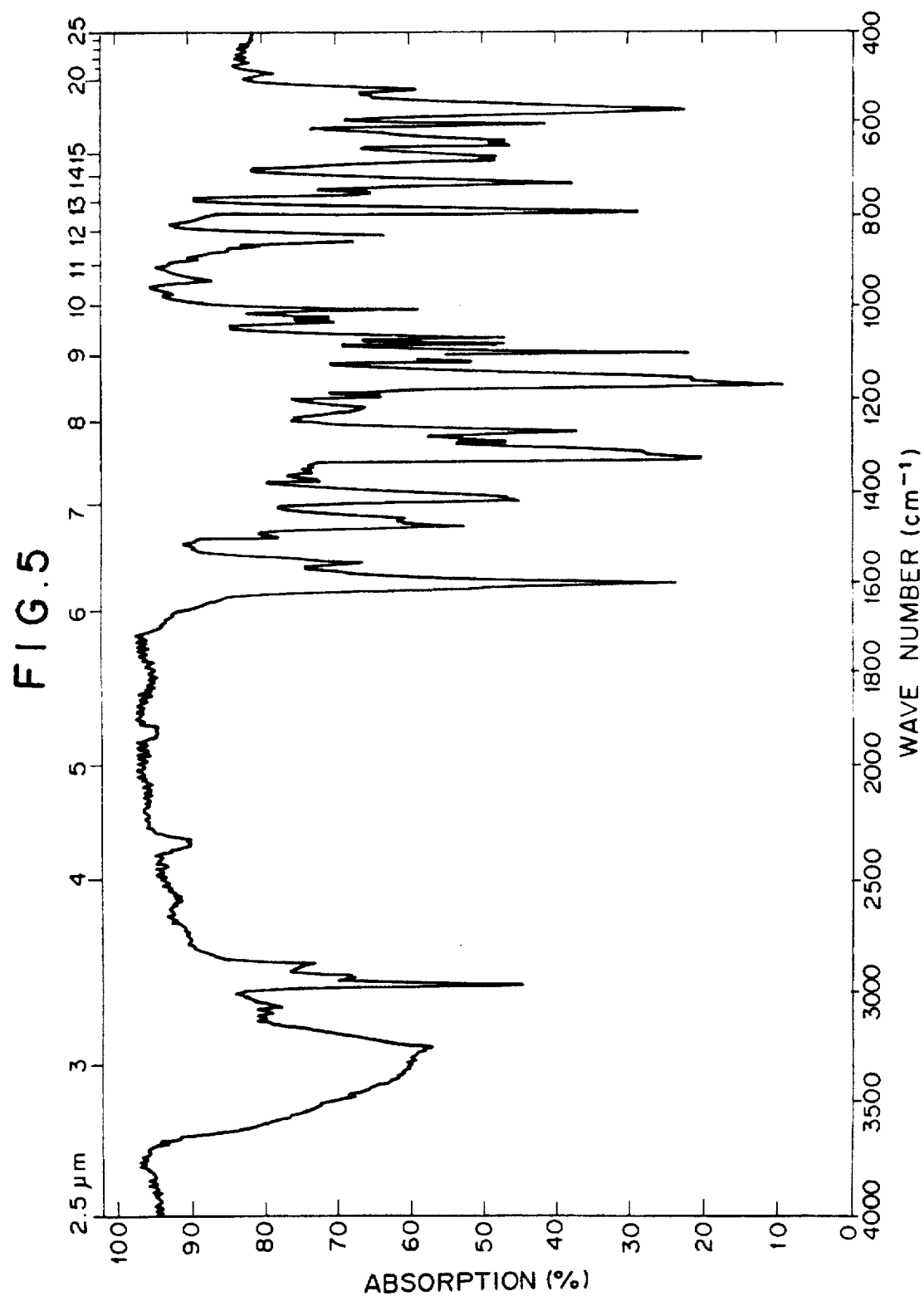
FIG. 5 is an infrared absorption spectrum of the compound obtained in Example 5.
Figure 6:
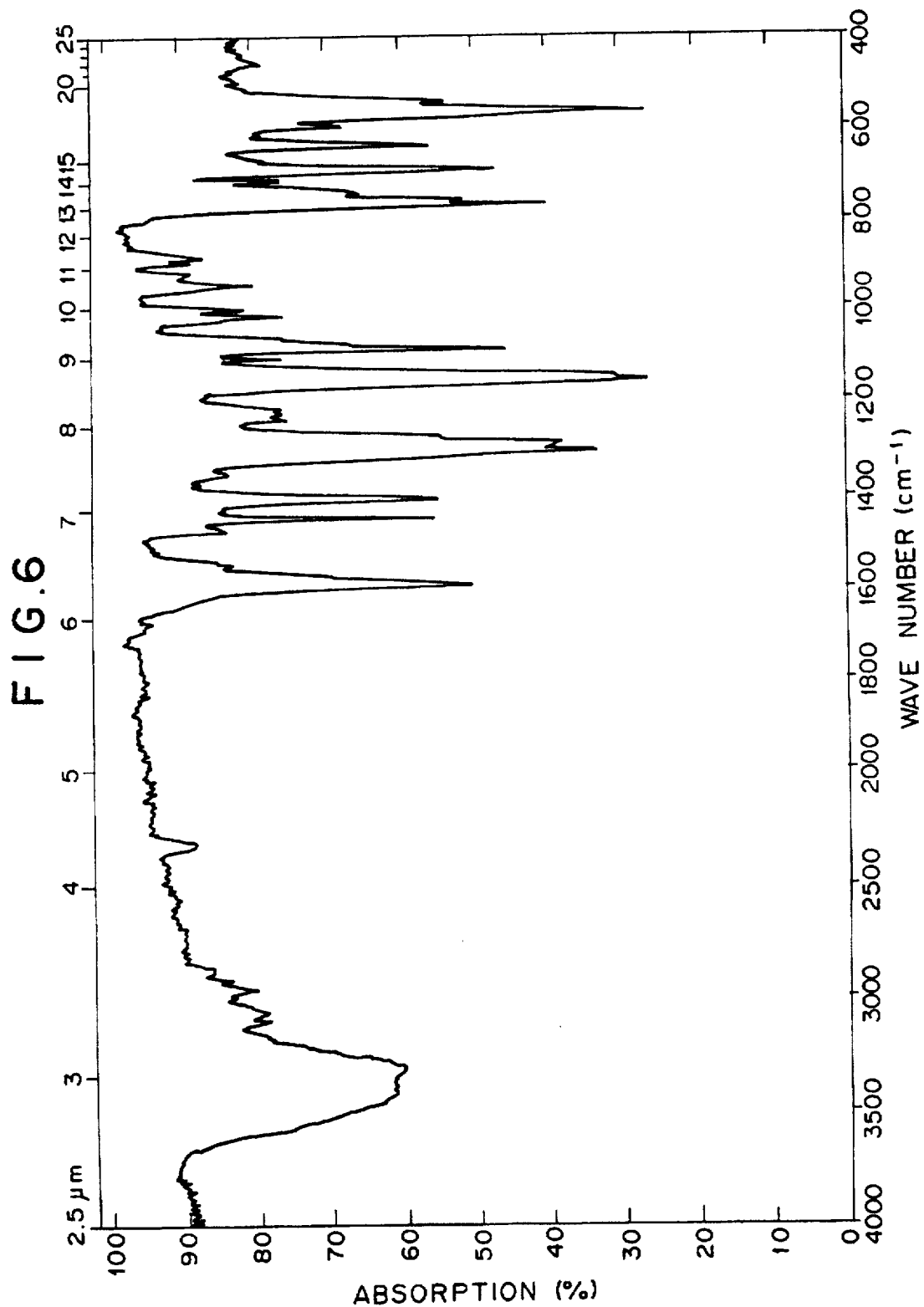
FIG. 6 is an infrared absorption spectrum of the compound obtained in Example 6.
Figure 7:
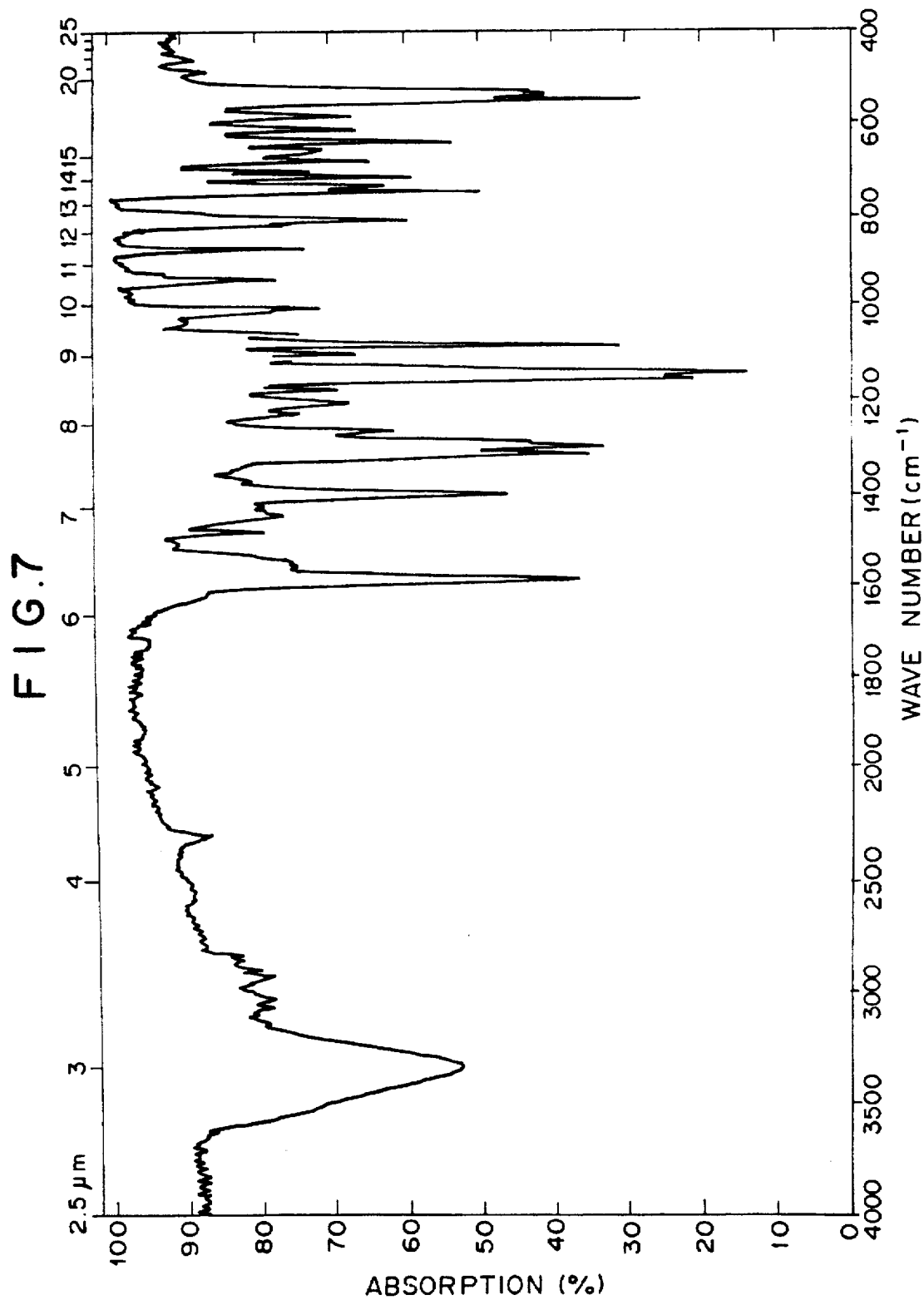
FIG. 7 is an infrared absorption spectrum of the compound obtained in Example 7.
Figure 8:
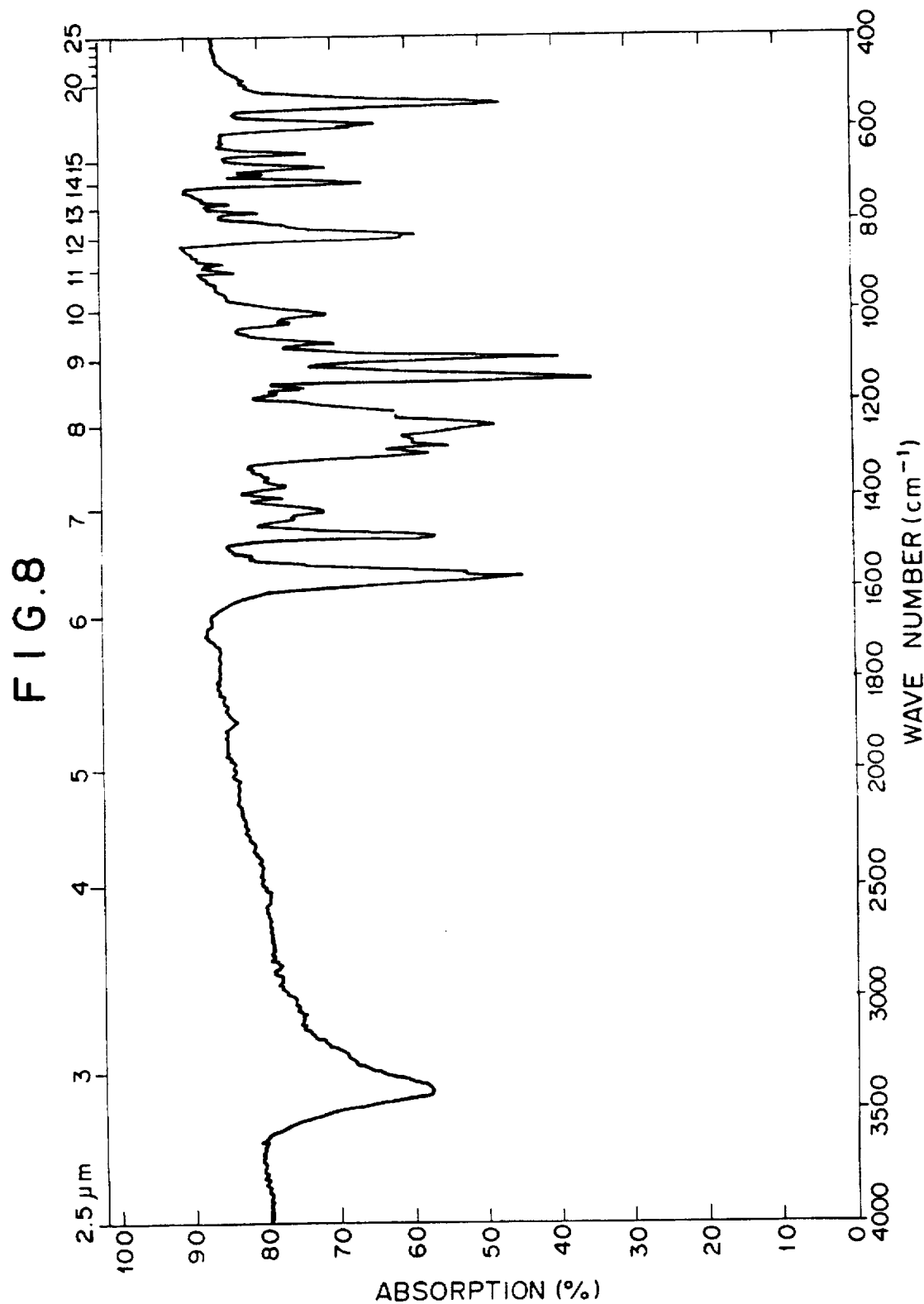
FIG. 8 is an infrared absorption spectrum of the compound obtained in Example 8.
Figure 9:
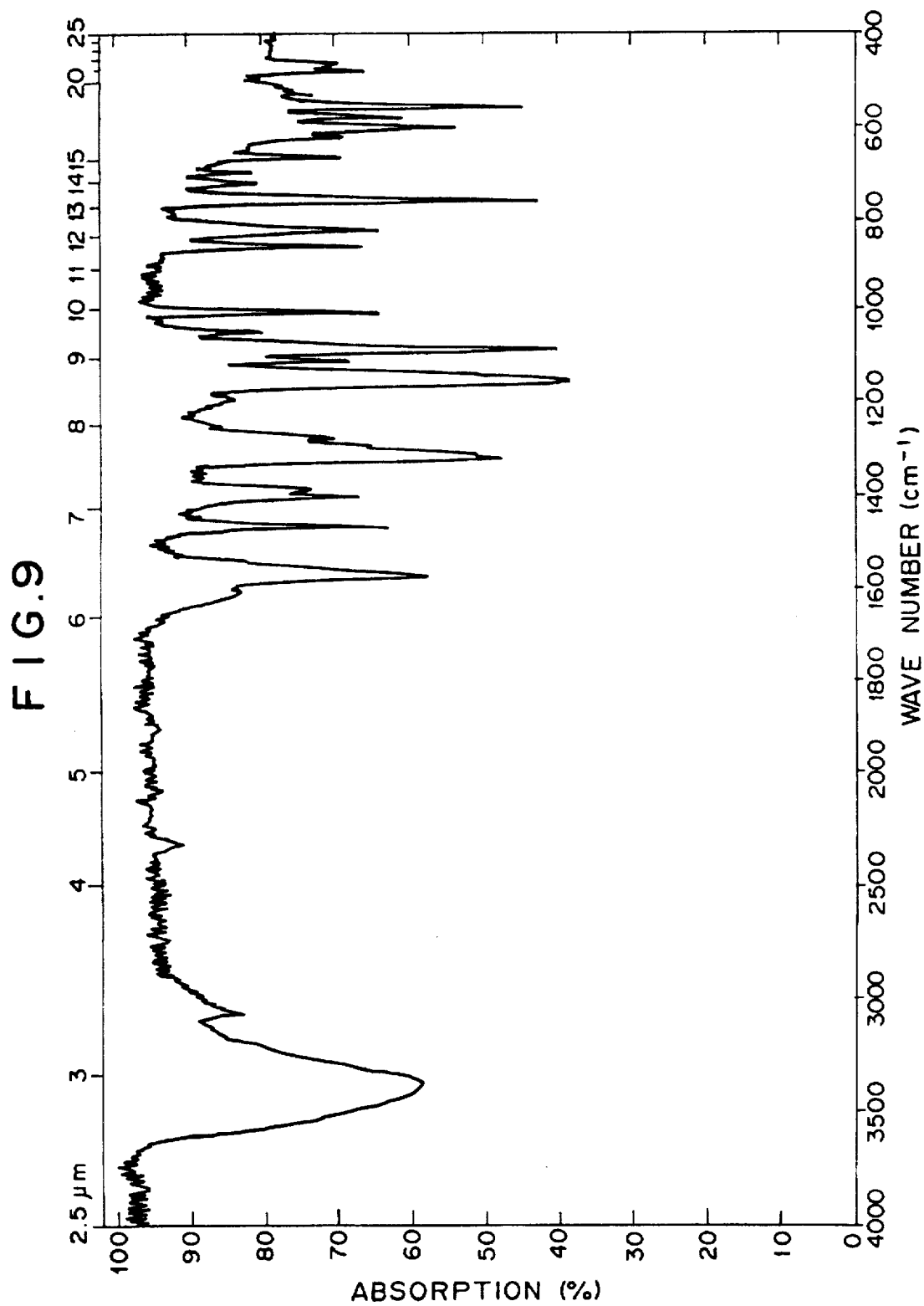
FIG. 9 is an infrared absorption spectrum of the compound obtained in Example 9.
Figure 10:
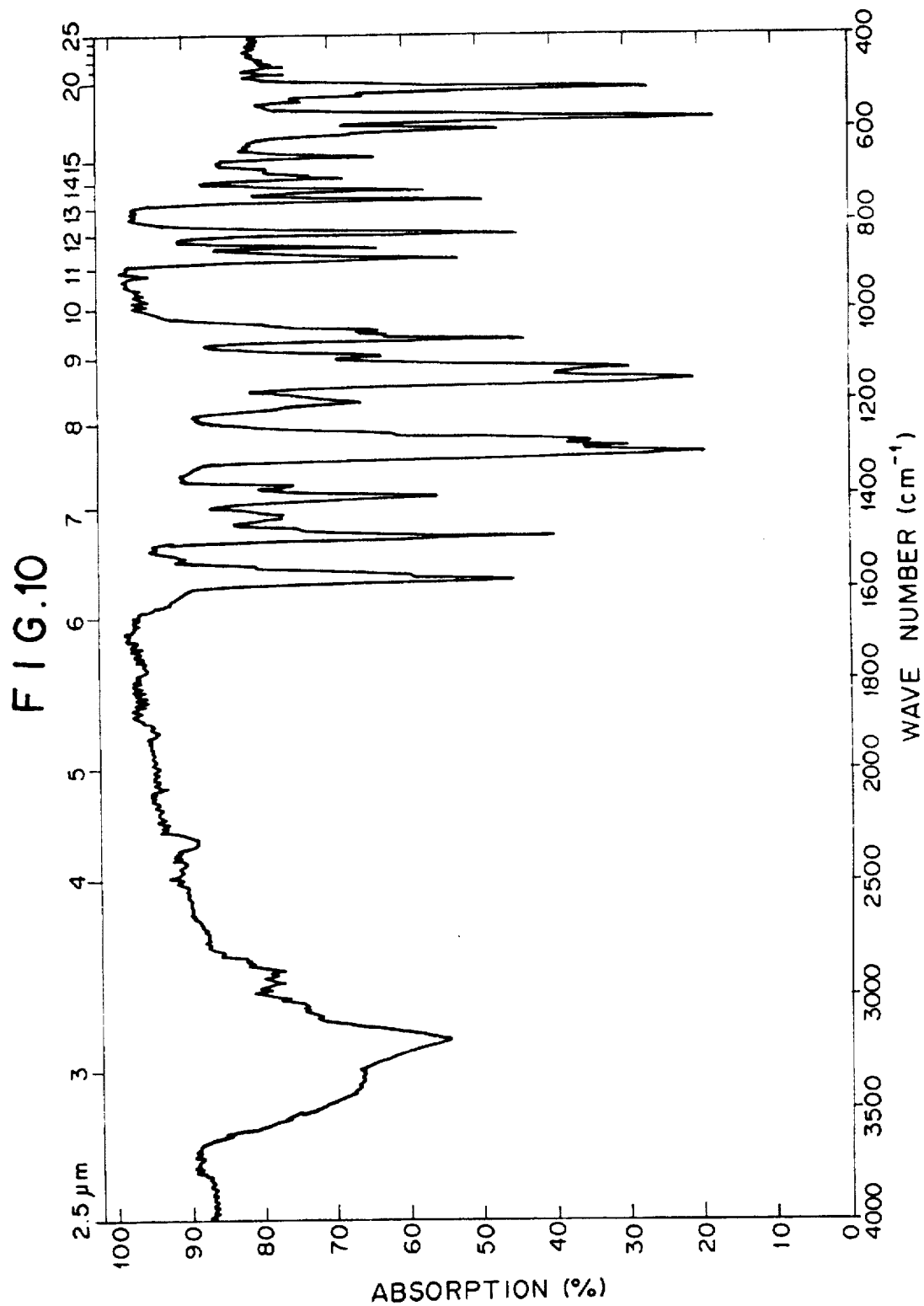
FIG. 10 is an infrared absorption spectrum of the compound obtained in Example 10.

The infrared absorption spectrum of the product is shown in FIG. 2.

EXAMPLES 3–10

The procedure of Example 2 was repeated with the exception that the compounds listed in Table 3 below were used in the given amounts in place of phenol, benzensulfonyl chloride, and methylisobutylketone used in Example 2. The results are shown in Table 4.

TABLE 3

| Ex. | Compound of formula (1) (g) | Compound of formula (7) (g) | Solvent for Recrystallization (liter) |
|---|---|---|---|
| 3 | phenol (94) | tosyl chloride (400) | methylisobutyl-ketone (1) |
| 4 | m-cresol (108) | benzenesulfonyl chloride (370) | n-buthanol (1) |
| 5 | m-cresol (108) | 4-isopropylbenzene-sulfonyl chloride (460) | toluene (1) |
| 6 | m-ethylphenol (122) | benzenesulfonyl chloride (370) | toluene (1) |
| 7 | m-ethylphenol (122) | tosyl chloride (400) | toluene (1) |
| 8 | phenol (94) | 2,4-dimethylbenzene-sulfonyl chloride (435) | toluene (1) |
| 9 | phenol (94) | 4-chlorobenzene-sulfonyl chloride (440) | toluene (1) |
| 10 | phenol (94) | 2,5-dimethylbenzene-sulfonyl chloride (435) | toluene (1) |

TABLE 4

| | | ($R_7$ = H) in general formula (1) | | Yield | m.p. | Infrared Absorption |
|---|---|---|---|---|---|---|
| Ex. | X | $R_1$, $R_4$ | $R_2$, $R_5$ | $R_3$, $R_6$ | (g) | (°C.) | Spectrum |
| 3 | H | H | 4-$CH_3$ | H | 340 | 170 | 3 |
| 4 | $CH_3$ | H | H | H | 330 | 189 | 4 |
| 5 | $CH_3$ | H | 4-$CH(CH_3)_2$ | H | 400 | 176 | 5 |
| 6 | $C_2H_5$ | H | H | H | 335 | 166 | 6 |
| 7 | $C_2H_5$ | H | 4-$CH_3$ | H | 300 | 180 | 7 |
| 8 | H | 2-$CH_3$ | 4-$CH_3$ | H | 320 | 105 | 8 |
| 9 | H | H | 4-Cl | H | 380 | 167 | 9 |
| 10 | H | 2-$CH_3$ | H | 5-$CH_3$ | 365 | 161 | 10 |

The infrared absorption spectrum of each of the products are shown in FIGS. 3–10.

EXAMPLE 11

A 2 liter reaction vessel was charged with 234 g of 4-(phenylsulfonyl)phenol, 60 g of tosyl chloride and 1 g of anhydrous ferric chloride. The charge was slowly heated with stirring to 100° C. in a nitrogen atmosphere. Generation of hydrochloric gas was weakened after conducting reaction for 5 hours, and then 150 g of tosyl chloride was dropped the same temperature for 5 hours. After that, the mixture was slowly heated to 150° C. and kept at this temperature for 24 hours to continue the reaction. Next, the reaction mixture thus obtained was poured into 1000 g of 5% aqueous sodium hydroxide solution, and the mixture was heated at 95° C. for 2 hours with stirring, and then filtered. The filtrate was then slowly dropped into 1000 g of 6% dilute sulfuric acid kept at 90° C. with stirring, thereby to obtain crystals. The crystals were filtered out, and after washed with 1 liter of water, dissolved in 1 liter of warm toluene, and then 100 ml of water was added to wash out an toluene oily component. The oily component was separated out, and further washed with 100 ml of water two times. Then, water in the oily component was removed by azeotropy, and the remaining component was subjected to decoloring by 3 g of activated carbon and 1 g of activated clay. The solution thus obtained was cooled to a room temperature to obtain 300 g of white crystal powder having a melting point of 158° C. From the results of the IR analysis, NMR analysis and elementary analysis (Table 5), it was confirmed that the product was 2-(4-methylsulfonyl)-4-(phenylsulfonyl)phenol.

TABLE 5

| Elementary Analysis Value (%) | C | H | S |
|---|---|---|---|
| Measured Value | 58.8 | 4.2 | 16.6 |
| Calculated Value (as $C_{18}H_{14}O_5S_2$) | 58.7 | 4.2 | 16.5 |

Figure 11:
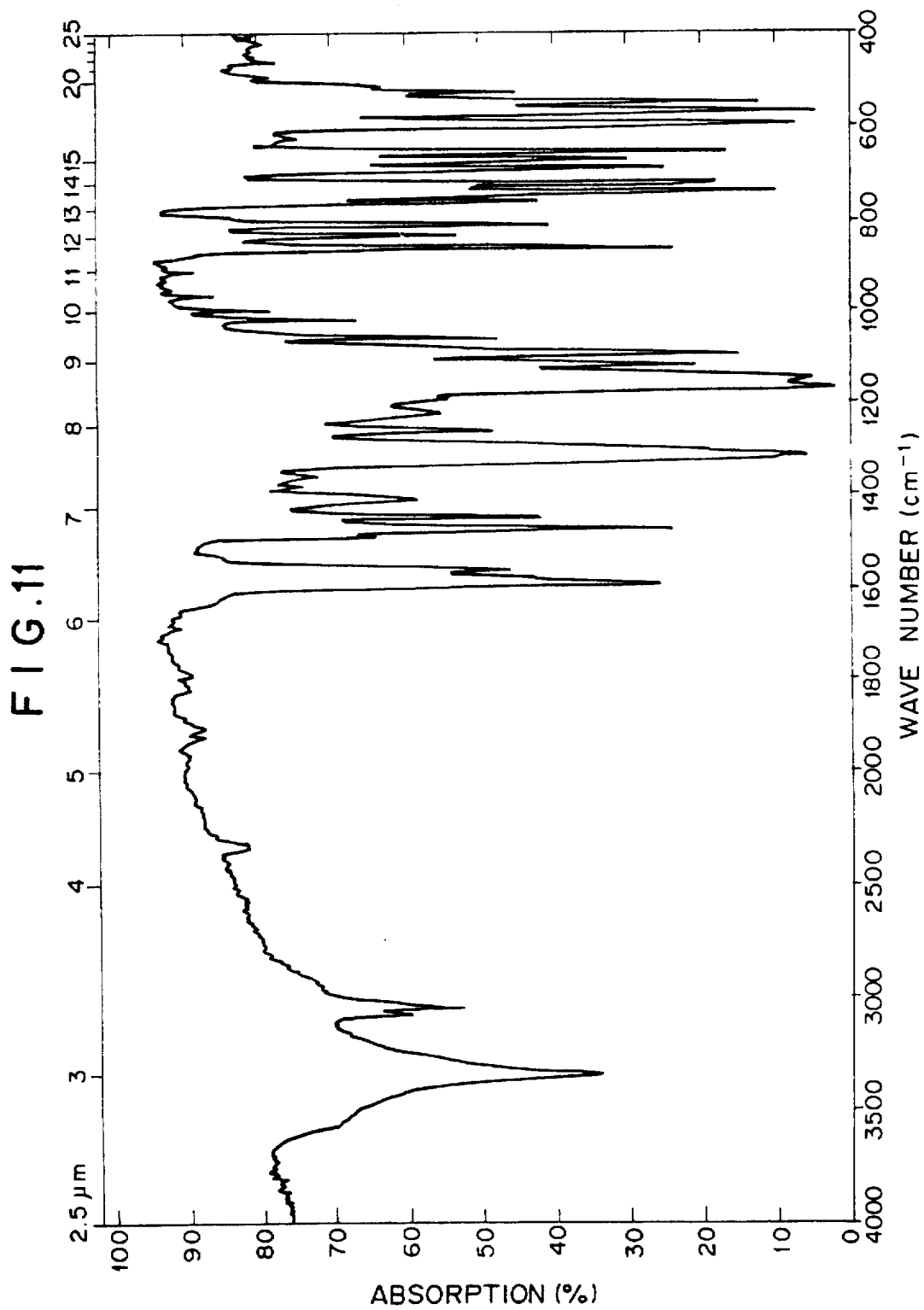
FIG. 11 is an infrared absorption spectrum of the compound obtained in Example 11.

The infrared absorption spectrum of the product is shown in FIG. 11.

EXAMPLE 12

An 1 liter reaction vessel was charged with 25 g of 4,4'-dihydoxydiphenyl sulfone, 180 g of benzenesulfonyl chloride and 0.1 g of anhydrous ferric chloride. The charge was slowly heated with stirring to 120° C. Generation of hydrochloric gas was weakened after conducting reaction for 24 hours and crystals were produced. The crystals were filtered out, and subjected to slurry washing using 500 ml of 5% aqueous sodium hydroxide solution and further washed with 1 liter of water. The crystals were recrystallized in 500 ml of a mixed solution of methanol:water=98:2 (in volume ratio) to obtain 30 g of white crystal powder having a melting point of 247° C. From the results of the IR analysis, NMR analysis and elementary analysis (Table 6), it was confirmed that the product was 4,4'-(dihydroxy-5,5'-bis (phenylsulfonyl)diphenylsulfone.

TABLE 6

| Elementary Analysis Value (%) | C | H | S |
|---|---|---|---|
| Measured Value | 54.4 | 3.4 | 17.9 |
| Calculated Value (as $C_{18}H_{14}O_5S_2$) | 54.3 | 3.4 | 18.1 |

Figure 12:
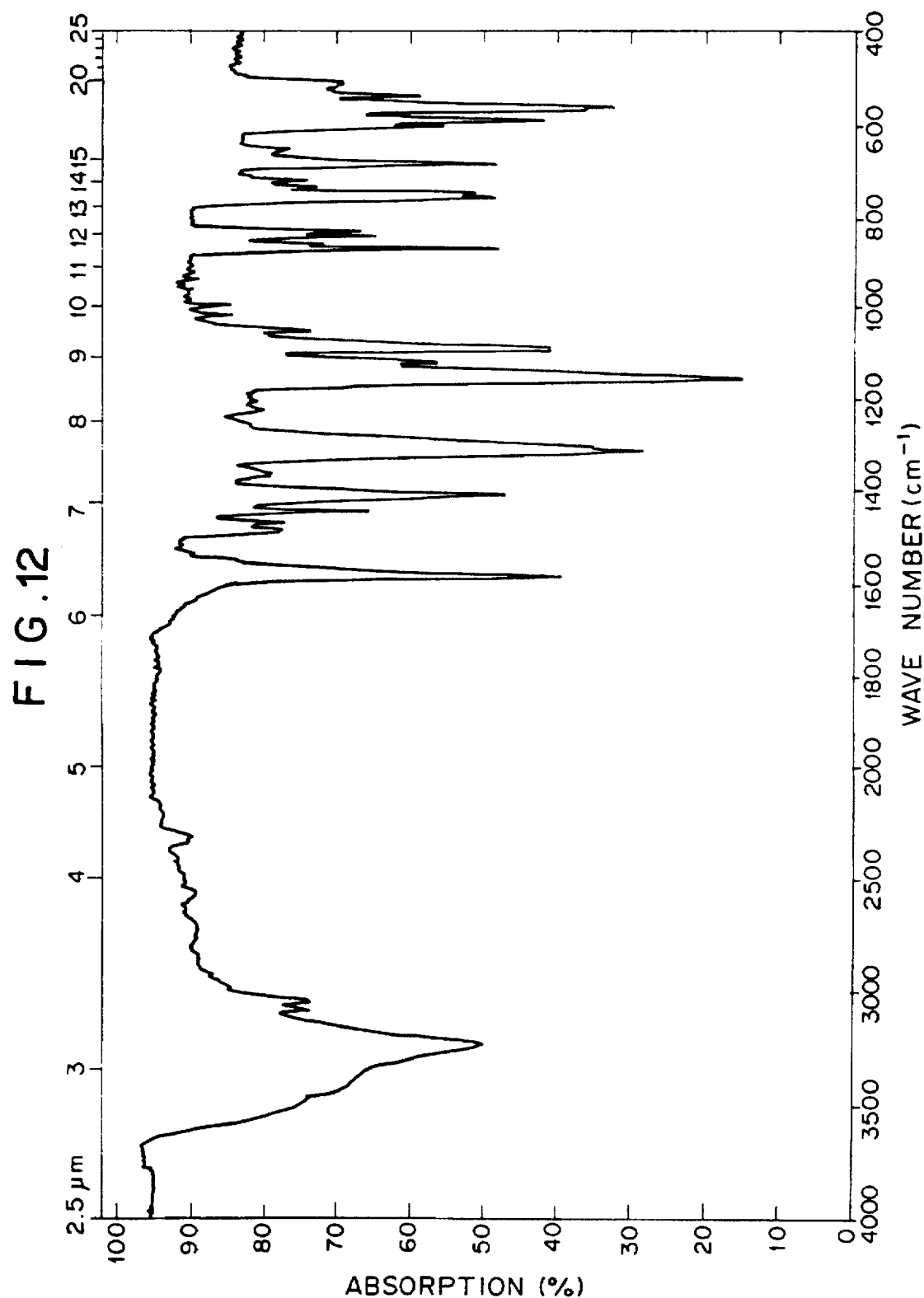
FIG. 12 is an infrared absorption spectrum of the compound obtained in Example 12.

The infrared absorption spectrum of the product is shown in FIG. 12.

EXAMPLE 13

Figure 13:
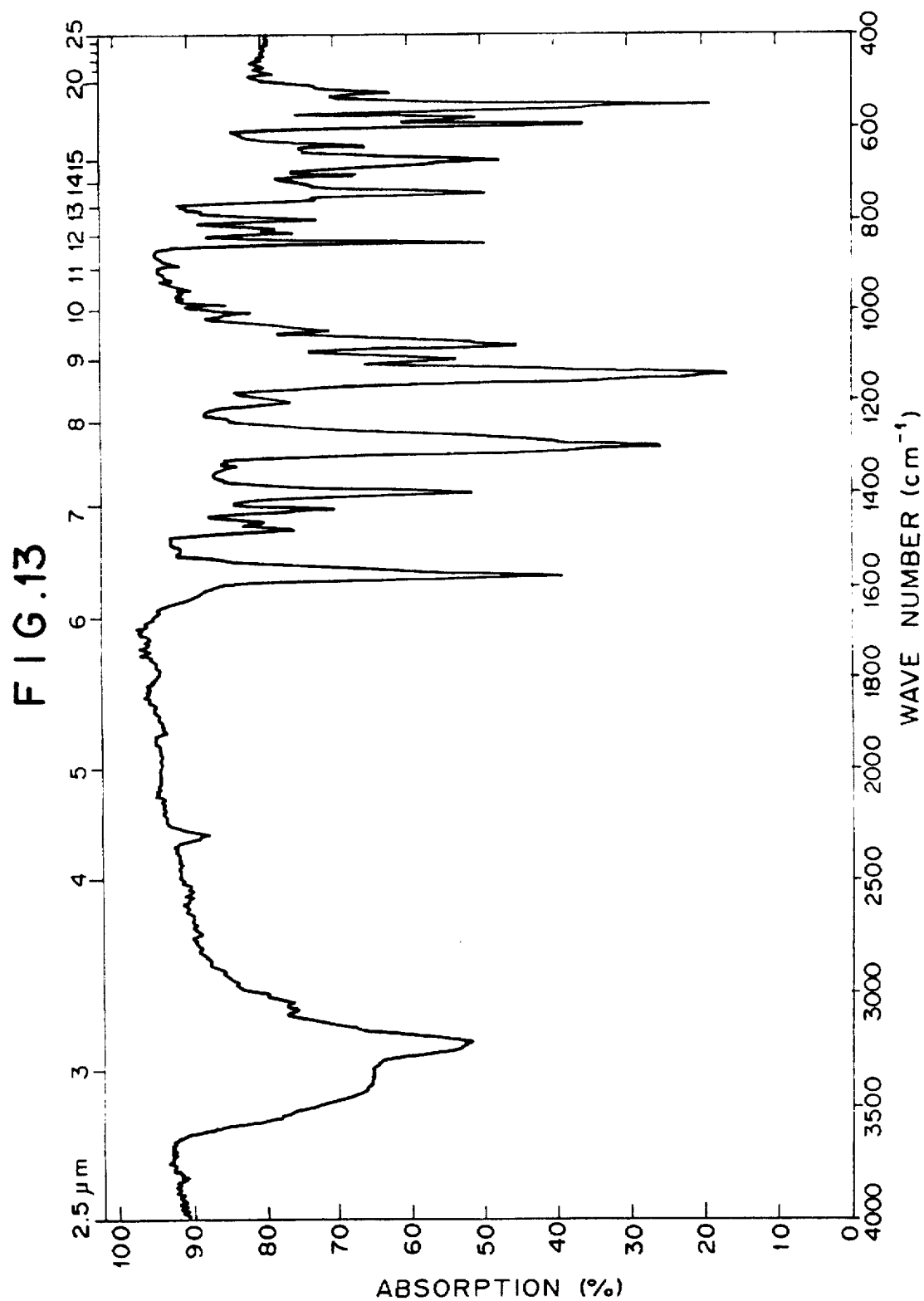
FIG. 13 is an infrared absorption spectrum of the compound obtained in Example 13.

The procedure of Example 11 was repeated with the exception that 248 g of 4-(4-methylphenylsulfonyl)phenol was used in place of 234 g of 4-(phenylsulfonyl)phenol, 60 g of benzenesulfonyl chloride in place of 60 g of tosyl chloride, and 134 g of benzenesulfonyl chloride in place of 150 g of tosyl chloride. The yield of the final product was 310 g, and its melting point was 155° C. The infrared absorption spectrum of the product is shown in FIG. 13. From the results of analysis, it was confirmed that the product was 2-(phenylsulfonyl)-4-(4-methylsulfonyl) phenol.

EXAMPLE 14

Figure 14:
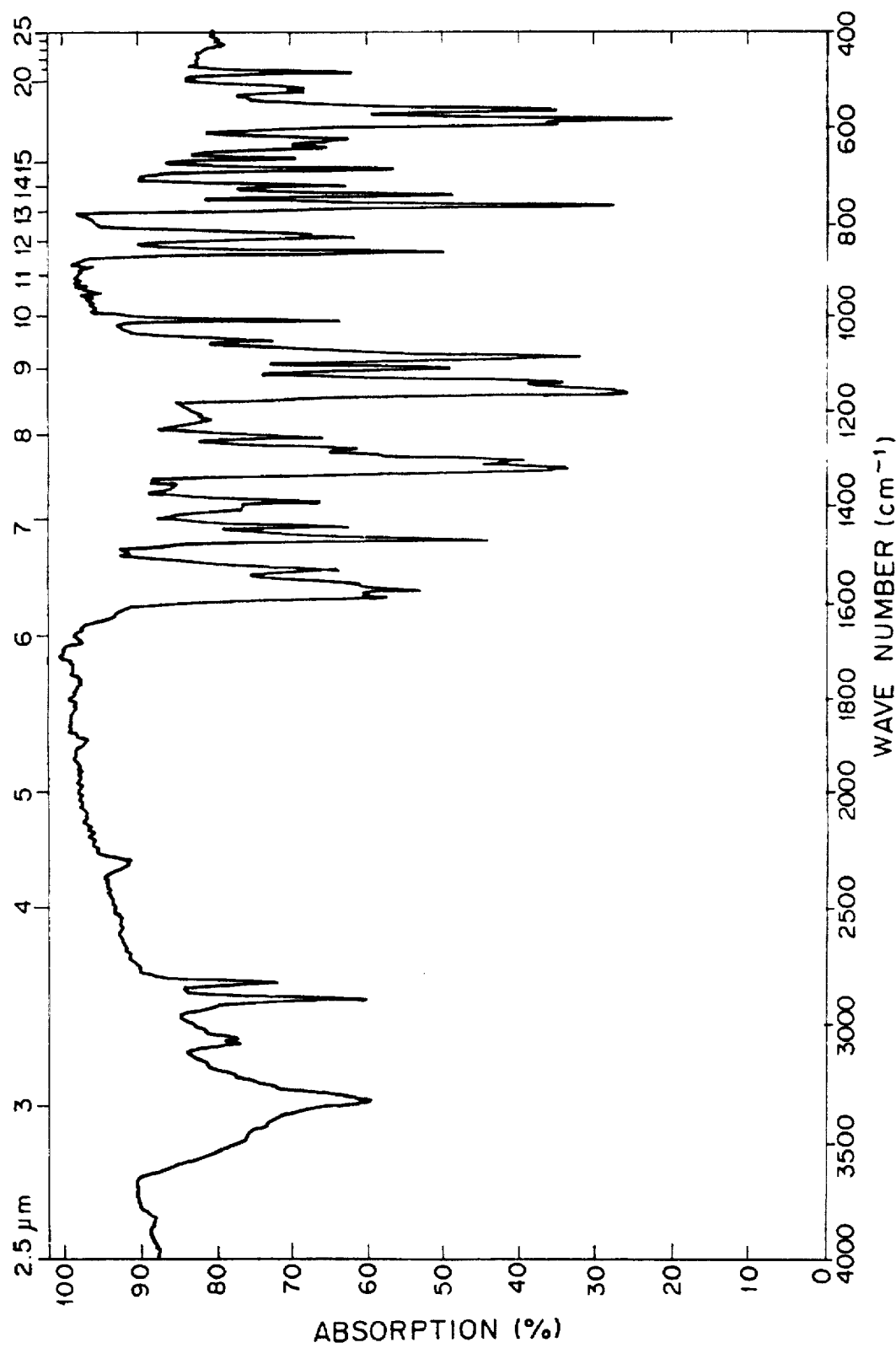
FIG. 14 is an infrared absorption spectrum of the compound obtained in Example 14.

The procedure of Example 11 was repeated with the exception that 60 g of 4-chlorobenzenesulfonylchloride in place of 60 g of tosyl chloride, and 172 g of 4-chlorobenzenesulfonylchloride in place of 150 g of tosyl chloride. The yield of the final product was 330 g, and its melting point was 135° C. The infrared absorption spectrum of the product is shown in FIG. 14. From the results of analysis, it was confirmed that the product was 2-(4-chlorophenylsulfonyl)-4-(phenylsulfonyl)phenol.

EXAMPLE 15

An 1 liter reaction vessel was charged with 50 g of 2,4-bis(phenylsulfonyl)phenol, 500 g of water and 107 g of 5% aqueous sodium hydroxide solution. The charge was stirred for 5 hours at 60° C., and then 250 g of 10% aqueous solution of zinc sulfonate (septohydrated) was dropped over 2 hours. After completion of the dropping, the mixture was kept at the same temperature for 2 hours for aging, and then the crystals were crystallized out. The crystals were washed with 1 liter of water, and then dried to obtain 52.5 g of white crystal powder. The product did not melt up to 250° C. From the results of the IR analysis and atomic absorption analysis, it was confirmed that the product was zinc salt of 2,4-bis (phenylsulfonyl)phenol.

The infrared absorption spectrum of the product is shown in FIG. 15.

EXAMPLE 16

An 1 liter reaction vessel was charged with 50 g of 2,4-bis(phenylsulfonyl)-5-ethylphenol, 500 g of water and 99 g of 5% aqueous sodium hydroxide solution and the charge was stirred for 5 hours at 60° C., and then 100 g of 10% aqueous solution of magnesium chloride was dropped over 2 hours. After completion of the dropping, the mixture was kept at the same temperature for 2 hours for aging, and then the crystals were crystallized out. The crystals were washed with 1 liter of water, and then dried to obtain 50 g of white crystal powder having melting point of 220° C.

From the results of the IR analysis and atomic absorption analysis, it was confirmed that the product was magnesium salt of 2,4-bis(phenylsulfonyl)-5-ethylphenol- The infrared absorption spectrum of the product is shown in FIG. 16.

EXAMPLE 17

Preparation of Basic Dye Dispersion 20 g of 3-N,N-dibutylamino-6-methyl-7-anilinofluorane was mixed with 80 g of 5% aqueous solution of polyvinyl alcohol (trade name "PVA-117", manufactured by Kurare Co., Ltd.) and finely pulverized in a ball mill for 20 hours, thereby to obtain a dispersion of the basic dye particles having an average particle size of 0.6 μm.

Preparation of Developer-Sensitizer Dispersion 20 g of 2,4-bis(4-metylphenylsulfonyl)phenol and 20 g of 1,2-bis(3-methylphonoxy)ethane were finely pulverized in 5% aqueous solution of polyvinyl alcohol ("PVA-117") using a ball mill for 20 hours, thereby to obtain a dispersion of the developer-sensitizer particles having an average particle size of 0.6 μm.

Preparation of Pigment Dispersion 30 g of calcium carbonate (trade name "UNIBAR 70", manufactured by Shiraishi Kogyo Co., Ltd.), 70 g of water and 1 g of 40% aqueous solution of sodium hexamethaphosphate were mixed together in a homogenizer with a rotation speed of 15,000 rpm for 15 min to obtain a pigment dispersion.

Preparation of Coating Liquid for Thermal Recording Layer 3 g of the basic dye dispersion, 6 g of the developer-sensitizer dispersion, 7 g of the pigment dispersion, 1.0 g of 30% HYDRIN Z-7 (trade name, manufactured by Chukyo Yushi Co., Ltd.) and 15 g of water were mixed together to obtain a coating liquid for a thermal recording layer.

Preparation of Thermal Recording Paper

On a substrate paper sheet the coating liquid was applied to form a thermal recording layer at 5 g/cm$^2$ on the dry basis using a wire bar, and dried in a oven at 60° C., and then calendared to have the smoothness of 200 (the Beck method).

EXAMPLES 18–35

The procedure of Example 17 was repeated with the exception that various developers listed in Table 7 below were used in place of 20 g of 2,4-bis(4-metylphenylsulfonyl) phenol. The kinds and the amounts used were given in Table 7.

TABLE 7

| Ex. | Developer | Amout Used (g) |
|---|---|---|
| 18 | 2,4-bis(phenylsulfonyl)phenol | 20 |
| 19 | 2,4-bis(2,5-dimethylphenylsulfonyl)phenol | 20 |
| 20 | 2,4-bis(phenylsulfonyl)-5-methylphenol | 20 |
| 21 | 2,4-bis(phenylsulfonyl)-5-ethylphenol | 20 |
| 22 | 2-(4-inethylphenylsulfonyl)-4-(phenylsulfonyl)phenol | 20 |
| 23 | 2-(4-chlorophenylsulfonyl)-4-(phenylsulfonyl)-phenol | 20 |
| 24 | 2-(phenylsulfonyl)-4-(4-methylphenylsulfonyl)phenol | 20 |
| 25 | 2,4-bis(phenylsulfonyl)phenol | 10 |
|  | 2,4-bis(phenylsulfonyl)-5-methylphenol | 10 |
| 26 | 2,4-bis(phenylsulfonyl)-5-methylphenol | 10 |
|  | 2,4-bis(4-ethylphenylsulfonyl)-5-ethylphenol | 10 |
| 27 | 2,4-bis(2,5-dimethylphenylsulfonyl)phenol | 10 |
|  | 2,4-bis(phenylsulfonyl)-5-methylphenol | 10 |
| 28 | 2,4-bis(2,5-dimethylphenylsulfonyl)phenol | 10 |
|  | 4,4'-dihydroxy-5-(phenylsulfonyl)-diphenylsulfone | 10 |
| 29 | 2,4-bis(2,5-diinethylphenylsulfonyl)phenol | 10 |
|  | 4,4'-dihydroxy-5,5'-bis(phenylsulfonyl)-diphenylsulfone | 10 |
| 30 | 2,4-bis(phenylsulfonyl)-5-methylphenol | 10 |
|  | 4-hydroxy-4'-isopropoxydiphenyl sulfone | 10 |
| 31 | 2,4-bis(2,5-dimethylphenylsulfonyl)phenol | 10 |
|  | 2,2-bis(4-hydroxyphenyl)propane | 10 |
| 32 | 2,4-bis(phenylsulfonyl)-5-ethylphenol | 10 |
|  | bis(3-aryl-4-hydroxyphenyl)sulfone | 10 |
| 33 | 2,4-bis(2,5-dimethylphenylsulfonyl)phenol | 8 |
|  | 2,4-bis(phenylsulfonyl)-5-methylphenol | 8 |
|  | 4-hydroxy-4'-isopropoxydiphenyl sulfone | 4 |
| 34 | 2,4-bis(phenylsulfonyl)phenol | 10 |
|  | Zn salt of 2,4-bis(phenylsulfonyl)phenol | 10 |
| 35 | 2,4-bis(2,4-dimethylphenylsulfonyl)phenol | 10 |
|  | Mg salt of 2,4-bis(phenylsulfonyl)-5-ethylphenol | 10 |

EXAMPLE 36

The procedure of Example 17 was repeated with the exception that a mixture of equal amount on the weight basis of developer-sensitizer dispersions obtained in Examples 17 and 20, respectively, was used.

EXAMPLE 37

The procedure of Example 17 was repeated with the exception that 20 g of a mixture of 2,4-bis(4-metylphenylsulfonyl)phenol and 2,4-bis(phenylsulfonyl)-5-methylphenol in the ratio of 50:50 on the weight basis.

COMPARATIVE EXAMPLES 1

The procedure of Example 17 was repeated with the exception that 20 g of 2,2-bis(4-hydorxyphenyl)propane was used, in place of 20 g of 2,4-bis(4-metylphenylsulfonyl) phenol.

COMPARATIVE EXAMPLES 2

The procedure of Example 17 was repeated with the exception that 10 g of 2,2-bis(4-hydorxyphenyl)propane and 10 g of 4-hydroxy-4'-isopropoxydiphnylsulfone were used, in place of 20 g of 2,4-bis(4-methylphenylsulfonyl)phenol.

The thermal recording paper sheets obtained in Examples 17–37 and Comparative Examples 1–2 were subjected to a printing test using a facsimile sold under the trade name "FF1700RX" in its copy mode.

Also, the following tests were conducted for evaluating the performance of the thermal recording paper sheets under the condition below:

Print Density: measured by Macbeth Densitometer

Thermal Resistance:

Background: measured by the naked eye after 24 hours at 60° C. according to the following criterion:
- ○: no change
- Δ: slight coloring
- x: significant coloring Printing: measure the percentage of the print density retention after 24 hours from printing at 60° C.

Print Density Retention (%)={(Print Density after 24 hrs)/(Density immediately after printing)}×100

Anti-humidity:

Background: measuring background blush of the not printed sheets stored for 24 hrs in 90% humidity and represented according to the standards of the background blush test.

Prints: measuring the percentage of the print density retention of the printed paper sheets stored for 24 hrs in 90% humidity.

Anti-plasticizer Property: measured according to the percentage of the retention for the thermal resistance under the condition that the sheets were wound on the outer periphery of a glass bottle, wrapping the wound sheets with three layers of a wrap ("HIWRAP V-450" manufactured by Mitsui Toatsu Kagaku Co., Ltd.) and kept 24 hrs at 40° C.

TABLE 8

| | | Heat Resistivity | | Anti-humidity | | Durability |
|---|---|---|---|---|---|---|
| | Density | Background Stain | Print Retention (%) | Background Stain | Print Retention (%) | against Plasticizer (%) |
| Ex. | | | | | | |
| 17 | 1.32 | ○ | 92 | ○ | 99 | 68 |
| 18 | 1.35 | ○ | 98 | ○ | 99 | 82 |
| 19 | 1.32 | ○ | 93 | ○ | 99 | 74 |
| 20 | 1.33 | ○ | 89 | ○ | 96 | 70 |
| 21 | 1.33 | ○ | 96 | ○ | 99 | 76 |
| 22 | 1.35 | ○ | 99 | ○ | 99 | 81 |
| 23 | 1.30 | ○ | 92 | ○ | 95 | 70 |
| 24 | 1.35 | ○ | 99 | ○ | 99 | 80 |
| 25 | 1.34 | ○ | 99 | ○ | 99 | 78 |
| 26 | 1.34 | ○ | 99 | ○ | 99 | 75 |
| 27 | 1.35 | ○ | 99 | ○ | 99 | 72 |
| 28 | 1.30 | ○ | 99 | ○ | 99 | 85 |
| 29 | 1.30 | ○ | 99 | ○ | 99 | 95 |
| 30 | 1.32 | ○ | 95 | ○ | 95 | 68 |
| 31 | 1.32 | ○ | 92 | ○ | 94 | 60 |
| 32 | 1.32 | ○ | 99 | ○ | 99 | 72 |
| 33 | 1.36 | ○ | 99 | ○ | 99 | 70 |
| 34 | 1.30 | ○ | 99 | ○ | 99 | 94 |
| 35 | 1.30 | ○ | 99 | ○ | 99 | 93 |
| 36 | 1.34 | ○ | 99 | ○ | 99 | 75 |
| 37 | 1.34 | ○ | 99 | ○ | 99 | 75 |
| Comparative Example | | | | | | |
| 1 | 1.30 | Δ | 63 | Δ | 65 | 10 |
| 2 | 1.32 | x | 70 | x | 75 | 20 |

As clearly understood from Table 8, the thermal recording media of the present invention is superior in developing property, and has less background blush with lapse of time, the stability of retaining the recorded image under high temperature and/or high humidity condition, and also a high anti-plasticizer property.

What is claimed is:

1. A thermal recording medium comprising a substrate and a thermal developer layer containing therein a developer using a developing reaction of an electron donative basic dye precursor and an electron receptive developer, said developer comprising at least one selected from the sulfonyl compounds represented by general formula (1) and the polyvalent metal salts thereof:

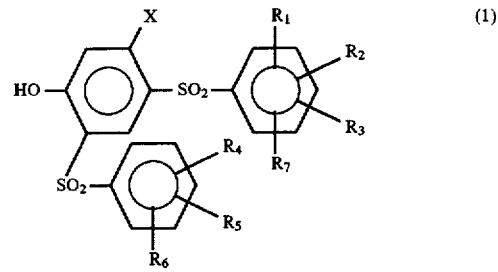

where X represents a hydrogen atom or a lower alkyl group, $R_1$, $R_2$ and $R_3$, which may be equal or different, represent a hydrogen atom, a hydroxyl group, a lower alkyl group or a cycloalkyl group, $R_4$, $R_5$ and $R_6$, which may be equal or different, represent a hydrogen atom, halogen atom, a lower alkyl group or a cycloalkyl group, and $R_7$, represents a hydrogen atom or

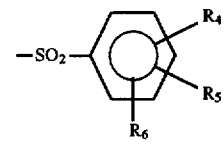

where $R_4$, $R_5$ and $R_6$ are defined above.

2. A thermal recording medium, comprised of a substrate and a thermal developer layer using a developing reaction of an electron donative basic dye precursor and an electron receptive developer, said developer comprising at least one selected from the sulfonyl compounds represented by general formula (1) and the polyvalent metal salts thereof:

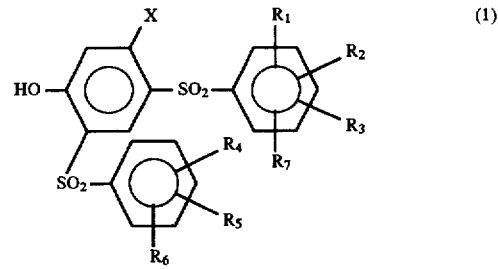

where X represents a hydrogen atom or a lower alkyl group, $R_1$, $R_2$ and $R_3$, which may be equal or different, represent a hydrogen atom, a hydroxyl group, a lower alkyl group or a cycloalkyl group, $R_4$, $R_5$ and $R_6$, which may be equal or different, represent a hydrogen atom, halogen atom, a lower alkyl group or a cycloalkyl group, and $R_7$ represents a hydrogen atom or

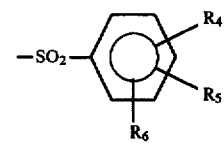

where $R_4$, $R_5$ and $R_6$ are defined above, and at least one selected from the diphenyl derivatives represented by general formula (2) below:

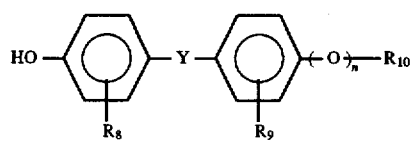
(2)
wherein $R_8$ and $R_9$, which may be equal or different, represent a hydrogen atom, a lower alkyl group or a lower alkylene group, and $R_{10}$ represents a hydrogen atom or straight or branched lower alkyl group, Y represents sulfonyl group, a lower alkylene group or a lower alkylidene group, and n represents 0 or 1.
* * * * *

UNITED STATES PATENT AND TRADEMARK OFFICE
CERTIFICATE OF CORRECTION

PATENT NO. : 5,705,452
DATED : January 6, 1998
INVENTOR(S) : Toranosuke Saito; Shigeru Oda; Eiji Kawabata It is certified that error appears in the above-indentified patent and that said Letters Patent is hereby corrected as shown below:

First page of patent under [73] "Assignee" : change "Haihatsu" to --Kaihatsu--.

Signed and Sealed this

Thirty-first Day of August, 1999

*Attest:*

Q. TODD DICKINSON

*Attesting Officer*  *Acting Commissioner of Patents and Trademarks*